(12) United States Patent
Hong

(10) Patent No.: US 10,859,789 B2
(45) Date of Patent: Dec. 8, 2020

(54) CURVED PATTERN MARKER AND OPTICAL TRACKING DEVICE INCLUDING MARKER

(71) Applicant: KOH YOUNG TECHNOLOGY INC., Seoul (KR)

(72) Inventor: Jong Kyu Hong, Anyang-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 134 days.

(21) Appl. No.: 16/087,253

(22) PCT Filed: Mar. 13, 2017

(86) PCT No.: PCT/KR2017/002655
§ 371 (c)(1),
(2) Date: Sep. 21, 2018

(87) PCT Pub. No.: WO2017/164552
PCT Pub. Date: Sep. 28, 2017

(65) Prior Publication Data
US 2019/0101719 A1    Apr. 4, 2019

(30) Foreign Application Priority Data

Mar. 22, 2016  (KR) .................. 10-2016-0034121
Feb. 8, 2017   (KR) .................. 10-2017-0017645

(51) Int. Cl.
*G02B 7/04*    (2006.01)
*B29D 11/00*   (2006.01)
(Continued)

(52) U.S. Cl.
CPC ............. *G02B 7/04* (2013.01); *A61B 34/20* (2016.02); *B29D 11/00* (2013.01); *G02B 5/126* (2013.01);
(Continued)

(58) Field of Classification Search
CPC . G02B 7/023; G02B 7/08; G02B 7/04; G02B 7/102; H02K 41/0356
(Continued)

(56) References Cited

U.S. PATENT DOCUMENTS 5,739,965 A * 4/1998 Ohno ................. G02B 9/04
                                         359/717
6,507,441 B1   1/2003 Eisenberg et al.
(Continued)

FOREIGN PATENT DOCUMENTS

CN   105142561   12/2015
EP   2 992 852   3/2016
(Continued)

OTHER PUBLICATIONS

Japanese Office Action for Japanese Application No. 2018-549948, with English translation, dated Sep. 17, 2019.
(Continued)

*Primary Examiner* — Mohammed A Hasan
(74) *Attorney, Agent, or Firm* — Kile Park Reed & Houtteman PLLC

(57) ABSTRACT

A technical concept of the present invention provides: a curved pattern marker capable of improving the precision of position detection and reducing size; and an optical tracking device including the marker. The marker comprises: a first lens unit, which has at least one lens having an incident surface, emits incident light within a target range, and is formed such that a light parallel to an optical axis among the incident light is vertically incident on the incident surface; a pattern unit having a curved pattern formed therein; and a second lens unit arranged between the first lens unit and the pattern unit, and adjusting the light emitted from the first lens unit such that the light is focused on the curved pattern.

16 Claims, 18 Drawing Sheets

Fine Pattern Surface

(51) Int. Cl.
    *G02B 27/34*   (2006.01)
    *A61B 34/20*   (2016.01)
    *G02B 27/30*   (2006.01)
    *G02B 5/126*   (2006.01)
    *G02B 9/04*    (2006.01)
    *G02B 9/12*    (2006.01)
    *G02B 27/09*   (2006.01)
    *G06K 9/00*    (2006.01)
    *G02B 27/32*   (2006.01)
    *G02B 17/08*   (2006.01)

(52) U.S. Cl.
    CPC .............. *G02B 9/04* (2013.01); *G02B 9/12* (2013.01); *G02B 27/0955* (2013.01); *G02B 27/30* (2013.01); *G02B 27/34* (2013.01); *G06K 9/00503* (2013.01); *G02B 17/0856* (2013.01); *G02B 27/32* (2013.01)

(58) Field of Classification Search
    USPC ........................................................ 359/822
    See application file for complete search history.

(56) References Cited

U.S. PATENT DOCUMENTS

| | | |
|---|---|---|
| 2005/0185283 A1 | 8/2005 | Belenkii et al. |
| 2007/0183041 A1* | 8/2007 | McCloy ............... G01S 5/16 359/515 |
| 2011/0233799 A1 | 9/2011 | Kang |
| 2013/0250284 A1 | 9/2013 | Lienhart et al. |
| 2014/0015997 A1* | 1/2014 | Baba ............... G02B 13/003 348/222.1 |
| 2016/0287341 A1 | 10/2016 | Hong et al. |
| 2018/0046835 A1 | 2/2018 | Hong et al. |
| 2019/0239963 A1 | 8/2019 | Hong et al. |

FOREIGN PATENT DOCUMENTS

| | | |
|---|---|---|
| FR | 574981 | 7/1924 |
| JP | 8-334684 | 12/1996 |
| JP | 2006-322910 | 11/2006 |
| JP | 2008-026731 | 2/2008 |
| JP | 2012-145559 | 8/2012 |
| JP | 2012/173026 | 12/2012 |
| JP | 2012-237966 | 12/2012 |
| JP | 2016-516526 | 6/2016 |
| KR | 10-0843453 | 7/2008 |
| KR | 10-2010-0029577 | 3/2010 |
| KR | 10-1406220 | 6/2014 |
| KR | 10-1487248 | 1/2015 |
| KR | 10-1627813 | 6/2016 |
| KR | 10-1820682 | 1/2018 |

OTHER PUBLICATIONS

Extended European Search report corresponding to European Patent Application No. 17770523.3, dated Oct. 23, 2019.

International Search Report for International Application No. PCT/KR2017/002655, dated Apr. 28, 2017.

Korean Office Action with English translation for Koran Application No. 10-2017-0017645, dated Dec. 15, 2017.

Chinese Office Action, with English translation, corresponding to Application No. or Publication No. 201780019244.6, dated Apr. 28, 2020.

* cited by examiner

Fine Pattern Surface

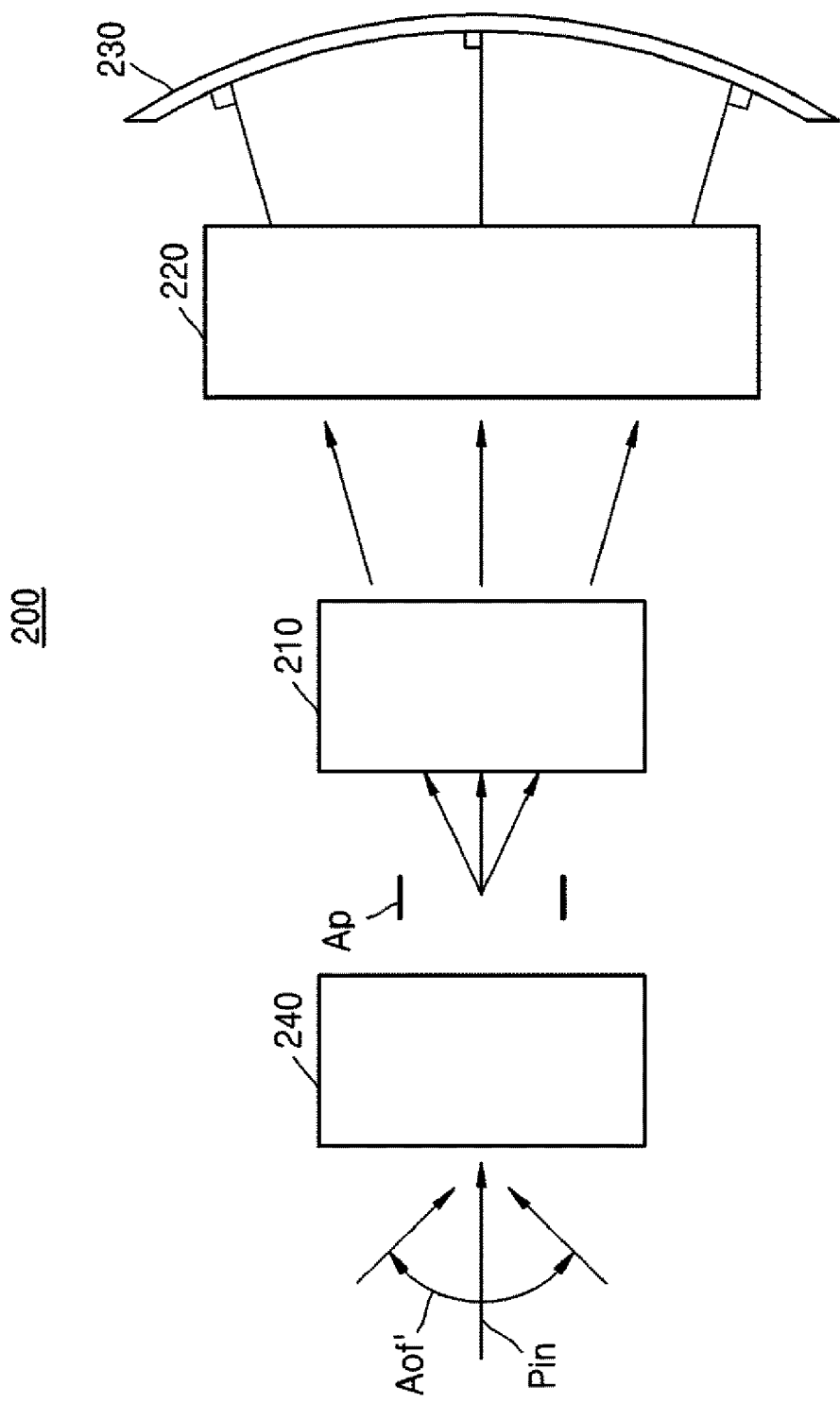

200a

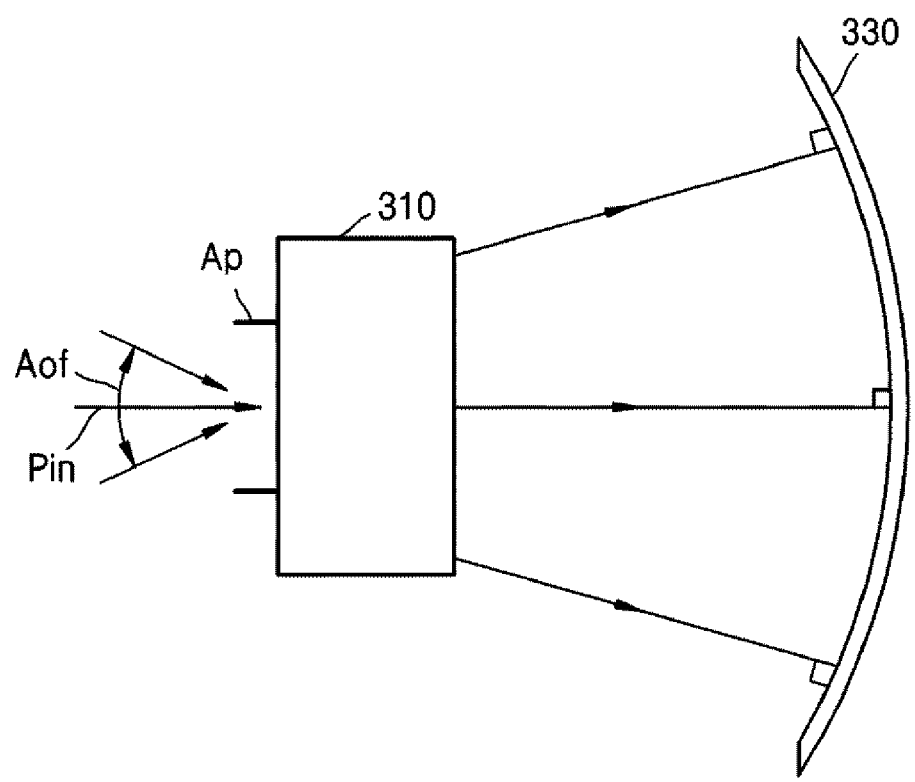

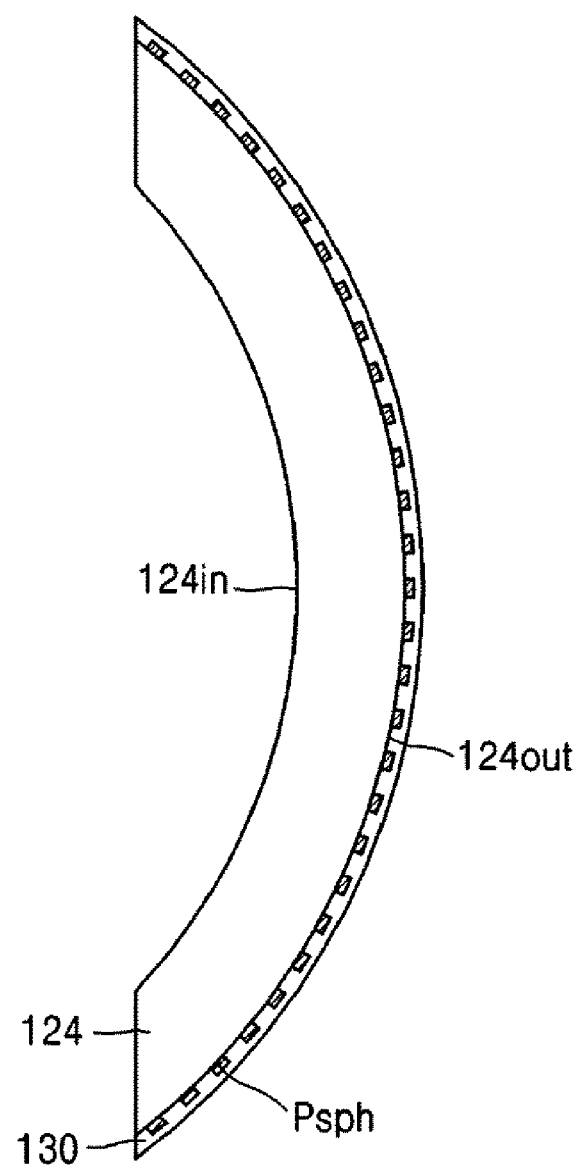

CURVED PATTERN MARKER AND OPTICAL TRACKING DEVICE INCLUDING MARKER

TECHNICAL FIELD

The technical idea of the present disclosure relates to a marker capable of tracking a position of an object and, more particularly, to a marker having a curved pattern and an optical tracking device including the marker.

BACKGROUND ART

In general, an optical tracking system may be used in order to track a position of an object. For example, an optical tracking system may be utilized in order to track an object in real time in an equipment such as a surgical robot. The optical tracking system generally includes a plurality of markers attached to an object and imaging units configured to image light reflected by the markers, and mathematically computes the information obtained from the imaging units so as to obtain position information and the like. The background art of the present disclosure is disclosed in "Marker for Measuring Position and Orientation" of Korean Patent Laid-Open Publication No. 10-1627813 (May 31, 2016), "Optical Tracking System" of Korean Patent Laid-Open Publication No. 10-1487248 (Jan. 22, 2015), and "Optical Tracking System and Tracking Method Using the Same" of Korean Patent Laid-Open Publication No. 10-1406220 (Jun. 3, 2014).

SUMMARY

The technical idea of the present disclosure is to provide a marker capable of improving a precision of position detection and reducing size, and an optical tracking device including the marker.

In order to solve the above problem, the technical idea of the present disclosure provides a curved pattern mark including: a first lens unit including at least one lens having an incident surface and configured to emit incident light within a target range, the first lens unit being formed such that a light parallel to an optical axis among the incident light is perpendicularly incident on the incident surface; a pattern unit having a curved pattern formed therein; and a second lens unit disposed between the first lens unit and the pattern unit, and configured to adjust the light emitted from the first lens unit such that the light emitted from the first lens unit is focused on the curved pattern.

In an embodiment of the present disclosure, the curved pattern marker may emit a light reflected from the pattern unit to be parallel to the incident light using the first lens unit and the second lens unit. In an embodiment of the present disclosure, the curved pattern marker may further include an aperture disposed in front of the incident surface of the first lens unit and configured to limit a cross-sectional area through which the light is incident on the incident surface of the first lens unit. In an embodiment of the present disclosure, the incident surface of the first lens unit is a plane parallel to an opening face of the aperture. In an embodiment of the present disclosure, the curved pattern marker may further include a third lens unit disposed in front of the aperture and configured to condense the incident light to the aperture.

In an embodiment of the present disclosure, the area of the emitting surface of the first lens unit may be larger than the area of the incident surface of the first lens unit. In an embodiment of the present disclosure, the area of the target range may be larger than the area of the emitting surface of the first lens unit and smaller than or equal to the incident surface of the second lens unit.

In an embodiment of the present disclosure, the first lens unit may include a first lens, a second lens, and a third lens sequentially coupled to each other in a direction toward the second lens unit, and the second lens unit may further include a fourth lens coupled to a curved lens in a direction toward the first lens unit.

In an embodiment of the present disclosure, the first lens unit may have a structure in which the incident surface of the second lens is coupled to the emitting surface of the first lens and the incident surface of the third lens is coupled to the emitting surface of the second lens, and the second lens unit may have a structure in which the incident surface of the curved lens is coupled to the emitting surface of the fourth lens, and the fourth lens may be disposed apart from the third lens.

In an embodiment of the present disclosure, an incident surface of the fourth lens may have a curvature smaller than a curvature of the emitting surface of the fourth lens, and the light emitted from the first lens unit may be focused on the curved pattern through the fourth lens and the curved lens.

In an embodiment of the present disclosure, an emitting surface of a curved lens has a curvature which is substantially equal to a curvature of the pattern unit, and the pattern unit may be bonded to the emitting surface of the curved lens.

In an embodiment of the present disclosure, a refractive index and a shape of incident surface and emitting surface of each of the first to fourth lenses and the curved lens are different from each other according to a curvature and a size of the curved pattern.

In an embodiment of the present disclosure, the first lens unit may include a first lens, a second lens, and a third lens sequentially coupled to each other in a direction toward the second lens unit, a curved lens may be disposed apart from the third lens, and a light emitted from the third lens may be focused on the curved pattern through the curved lens.

In an embodiment of the present disclosure, the curved pattern marker may further include a third lens unit disposed in a first direction opposite to a direction in which the second lens unit is disposed with respect to the first lens unit and including at least one lens, and a fourth lens unit disposed in the first direction from the third lens unit.

In an embodiment of the present disclosure, the third lens unit may include a fifth lens and a sixth lens sequentially coupled in the first direction, and the fourth lens unit may include a seventh lens disposed apart from the fifth lens in the first direction.

In an embodiment of the present disclosure, the curved pattern marker may further include a holder configured to accommodate the first lens unit and the second lens unit, and the pattern unit may be bonded to an emitting surface of a curved lens or may be bonded to an inner surface of the holder that faces the emitting surface of the curved lens.

In an embodiment of the present disclosure, the pattern unit may include an adhesive layer, a pattern layer on which the curved pattern is formed, and a reflective layer.

In addition, in order to solve the problem described above, a technical idea of the present disclosure provides a curved pattern marker including: a first lens unit including at least one lens having an incident surface and configured to emit incident light within a target range, the first lens unit being formed such that a light parallel to an optical axis among the incident light is perpendicularly incident on the incident surface; and a pattern unit disposed apart from the first lens unit and having a curved pattern on which a light emitted from the first lens unit is focused. A light reflected from the pattern unit is emitted to be parallel to the incident light using the first lens unit.

In an embodiment of the present disclosure, the curved pattern marker may further include an aperture disposed in front of the incident surface of the first lens unit and configured to limit a cross-sectional area through which the light is incident on the incident surface of the first lens unit, and a second lens unit disposed in front of the aperture and configured to condense the incident light to the aperture.

Further, in order to solve the problem described above, a technical idea of the present disclosure provides a curved pattern marker including: an aperture configured to limit a cross-sectional area of incident light; a first lens unit disposed in a first direction with respect to the aperture, including at least one lens having an incident surface, and configured to emit incident light within a target range, the first lens unit being formed such that a light passing through the aperture to be parallel to an optical axis among the incident light is perpendicularly incident on the incident surface; a second lens unit disposed in the first direction from the first lens unit and including a curved lens configured to perpendicularly emit a light component passing through a center of the aperture; a pattern unit disposed in the first direction from an emitting surface of the curved lens and having a curved pattern formed therein; and a holder configured to accommodate the first lens unit, the second lens unit, and the pattern unit.

In an embodiment of the present disclosure, the pattern unit may be bonded to the emitting surface of the curved lens. In an embodiment of the present disclosure, the pattern unit may be spaced apart from the emitting surface of the curved lens. In an embodiment of the present disclosure, the curved pattern marker may further include a third lens unit disposed in front of the aperture and configured to condense the incident light to the aperture.

In an embodiment of the present disclosure, the first lens unit may include a first lens, a second lens, and a third lens sequentially coupled to each other in a direction toward the second lens unit, and the second lens unit may further include a fourth lens coupled to the curved lens in a direction toward the first lens unit.

In an embodiment of the present disclosure, the curved pattern marker may further include a third lens unit disposed in a second direction opposite the first direction with respect to the aperture, and a fourth lens unit disposed in the second direction from the third lens unit.

Meanwhile, in order to solve the problem described above, a technical idea of the present disclosure provides an optical tracking device comprising: a curved pattern marker comprising: a first lens unit including at least one lens having an incident surface and formed such that a light parallel to an optical axis among the incident light is perpendicularly incident on the incident surface thereof; and a pattern unit having a curved pattern formed therein such that a light emitted from the first lens unit is focused on the curved pattern, in which the curved pattern and configured to emit a light reflected from the curved pattern in the form of parallel light; at least one image-forming unit configured to receive the parallel light for the curved pattern and to form an image as an enlarged pattern image; and a processor configured to analyze the pattern image and to calculate a position and a orientation of the curved pattern marker.

In an embodiment of the present disclosure, the curved pattern marker may further include an aperture disposed in front of the incident surface of the first lens unit and configured to define a cross-sectional area through which the light is incident on the incident surface of the first lens unit, and a second lens unit disposed in front of the aperture and configured to condense the incident light to the aperture.

In an embodiment of the present disclosure, the curved pattern marker may further include a second lens unit disposed between the first lens unit and the pattern unit, and configured to adjust the light emitted from the first lens unit such that the light emitted from the first lens unit is focused on the curved pattern. In an embodiment of the present disclosure, the curved pattern marker may further include an aperture disposed in front of the incident surface of the first lens unit and configured to define a cross-sectional area through which the light are incident on the incident surface of the first lens unit, and a third lens unit disposed in front of the aperture and configured to condense the incident light to the aperture.

In an embodiment of the present disclosure, the first lens unit may include a first lens, a second lens, and a third lens sequentially coupled to each other in a direction toward the second lens unit, and the second lens unit may further include a fourth lens coupled to the curved lens in a direction toward the first lens unit.

In an embodiment of the present disclosure, the curved pattern marker may further include a third lens unit disposed in a first direction opposite a direction in which the second lens unit is disposed with respect to the first lens unit and including at least one lens, and a fourth lens unit disposed in the first direction from the third lens unit.

A curved pattern marker according to the technical idea of the present disclosure includes a first lens unit, a second lens unit, and a pattern unit having a curved pattern. Thus, a light may be incident on the curved pattern portion in the pattern unit so as to be focused thereon, and the curved pattern may be emitted in the form of parallel light through reflection of light.

Further, a curved pattern marker according to the technical idea of the present disclosure emits the curved pattern by reflected light and does not require a separate light source. In addition, since a pattern unit including a curved pattern is disposed by being bonded to the curved lens disposed at the outermost position, a separate physical device for the arrangement of the curved pattern may be unnecessary.

Further, a curved pattern marker according to the technical idea of the present disclosure is able to contribute to the reduction of the size of the lenses based on the use of the curved pattern, and the reduction of the size of the marker. In addition, the lens unit is configured such that light is directly incident through the aperture Ap such that the position of entrance pupil relative to the angle of view is maintained to be constant. Thus, it is possible to minimize a position detection error of the marker.

On the other hand, by including the curved pattern marker, the optical tracking device according to the technical idea of the present disclosure is able to reduce the size of the entire device as well as to reduce the size of the marker. Further, the precision of position and orientation detection of an object may be improved.

BRIEF DESCRIPTION OF THE DRAWINGS

FIG. 6 is a conceptual view of a structure of a curved pattern marker according to an embodiment of the present disclosure;

FIG. 8 is a conceptual view of a structure of a curved pattern marker according to an embodiment of the present disclosure;

FIGS. 10A and 10B are cross-sectional views illustrating an arrangement structure of a pattern unit in curved pattern markers according to embodiments of the present disclosure;

DETAILED DESCRIPTION

Figure 1:
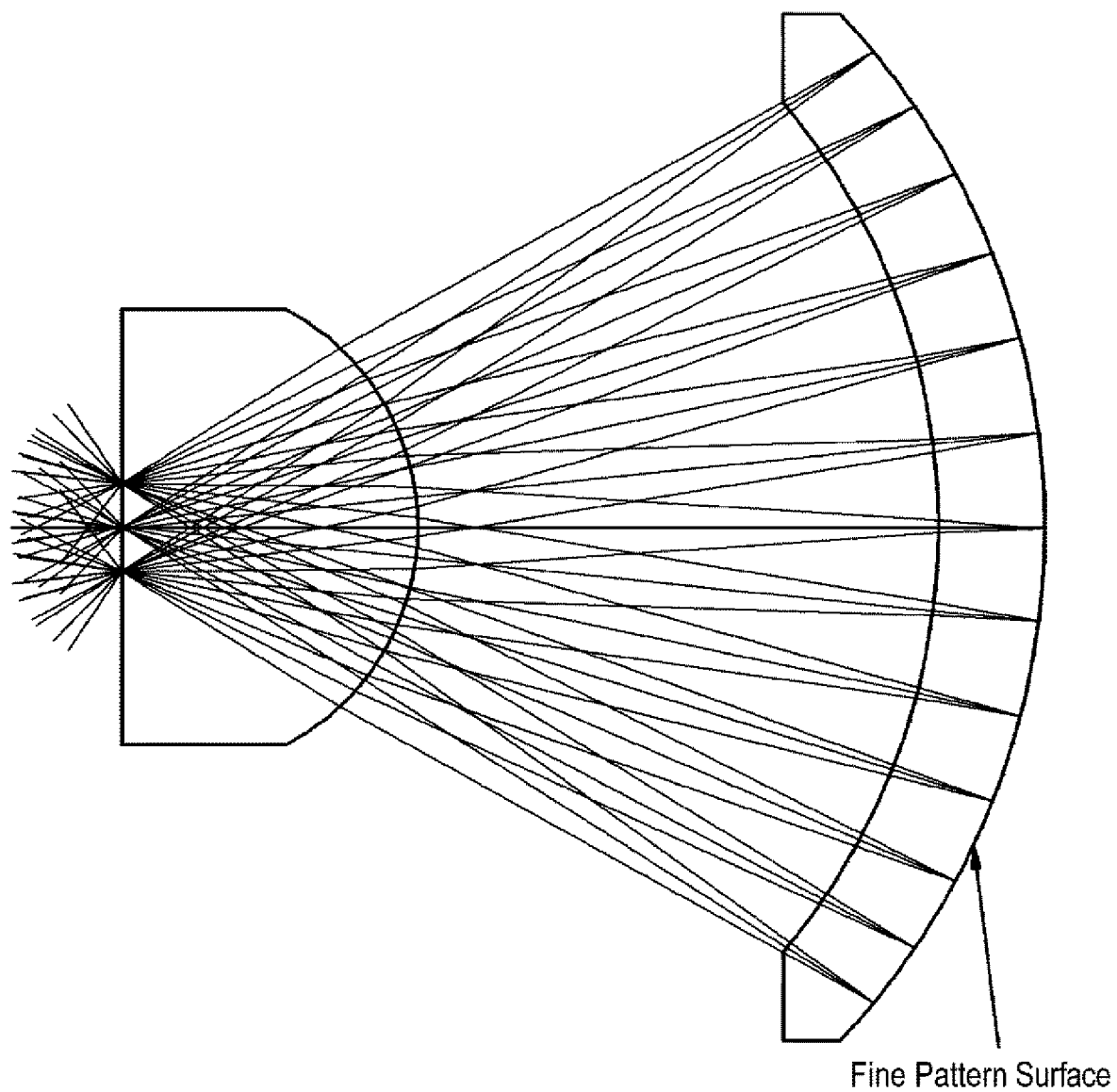
FIG. 1 is a view for explaining an optical effect obtained when an optical lens manufactured by a method according to the present disclosure includes micro-patterns on the inside of a curved surface thereof.

Hereinafter, embodiments of the present disclosure will be described in detail with reference to the accompanying drawings. Embodiments of the present disclosure are provided in order to more fully describe the present disclosure to those skilled in the art. The following embodiments can be modified in various forms, and the scope of the present disclosure is not limited to the following embodiments. Rather, these embodiments are provided in order to make this disclosure more full and complete, and to fully convey the technical idea of the disclosure to those skilled in the art.

In the following description, when an element is described as being connected to another element, the element may be directly connected to another element, but a third element may also be interposed therebetween. Similarly, when an element is described as existing above another element, the element may exist directly on the other element, and a third element may also be interposed therebetween. In addition, the structure or size of each constituent element in the drawings is exaggerated for convenience of explanation and clarity of explanation, and parts not relevant to the explanation were omitted. In the drawings, the same reference numeral refers to the same element. Meanwhile, the terms used herein are merely used for the purpose of describing the present disclosure and not for the purpose of limiting the meaning or the scope of the present disclosure described in the claims.

FIG. 1 is a view for explaining an optical effect obtained when an optical lens manufactured by a method according to the present disclosure includes micro-patterns on the inside of a curved surface thereof.

Referring to FIG. 1, an optical lens manufactured by a method according to the present disclosure may include micro-patterns on the inside of a curved surface thereof and form an appropriate reflective layer, thereby obtaining an optical phenomenon similar to a retroreflector in which light incident from the inside of the curved surface is reflected again. At this time, since the micro-patterns are provided on the reflecting surface on the inside of the curved surface, fine patterns obtained by reducing and condensing a shape of the micro-patterns may be obtained between a focus determined by an R value of the inner curved surface of the optical lens and the reflecting surface.

Figure 2:
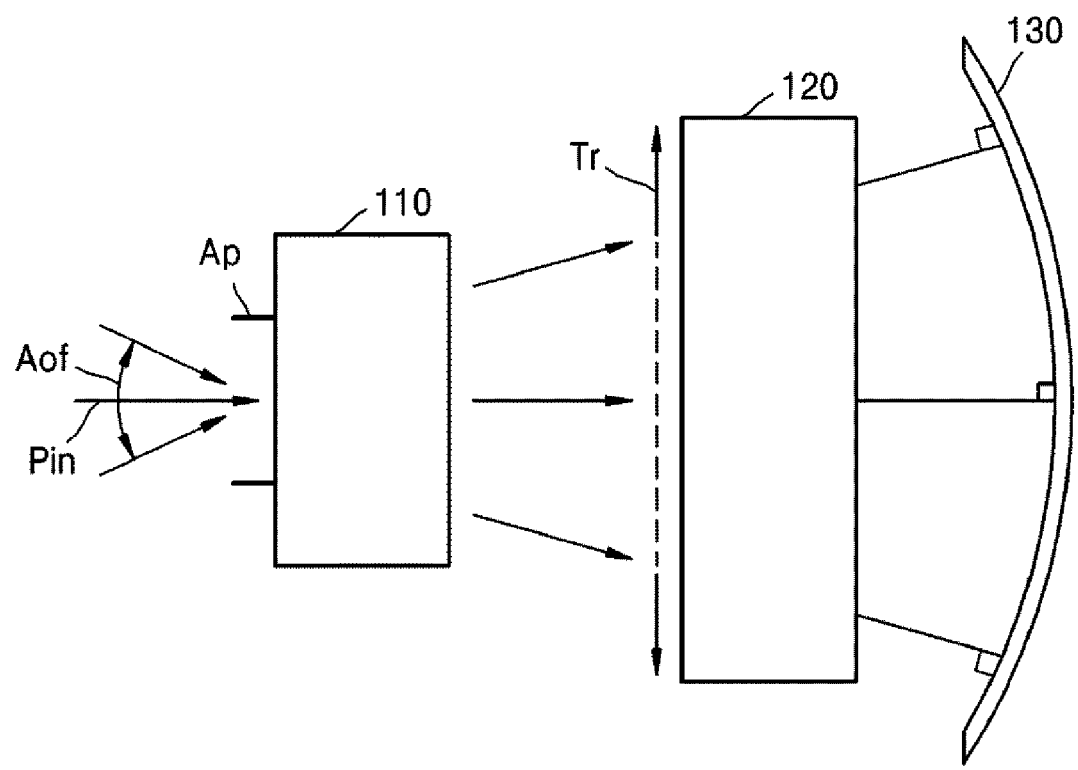
FIG. 2 is a conceptual view of a structure of a curved pattern marker according to an embodiment of the present disclosure.

FIG. 2 is a conceptual view of a structure of a curved pattern marker according to an embodiment of the present disclosure.

Referring to FIG. 2, a curved pattern marker 100 of the present embodiment may include a first lens unit 110, a second lens unit 120, and a pattern unit 130.

The first lens unit 110 may include at least one lens and may emit a light incident through an aperture Ap, that is, an incident light Pin, to the second lens unit 120. Here, the aperture Ap is a kind of opening through which light incident on the first lens unit 110 passes, and the amount of the light incident on the first lens unit 110 may be adjusted by the aperture Ap. In the curved pattern marker 100 of the present embodiment, the exposure area of the first lens unit 110 by the aperture Ap may be fixed. However, the present disclosure is not limited thereto, and the exposure area of the first lens unit 110 by the aperture Ap may be changed by adjusting the aperture Ap. In an embodiment, the aperture Ap may be disposed in front of an incident surface of the first lens unit 110 and limit a cross-sectional area through which the incident light Pin is incident on the incident surface of the first lens unit 110. In one embodiment, the aperture Ap may limit the cross-sectional area through which the incident light Pin is incident so that light emitted from the first lens unit 110 is emitted within a target range Tr.

The first lens unit 110 may emit the incident light Pin within the target range Tr by refracting the incident light Pin through lenses. Here, the target range Tr may be included in the incident surface of the first lens which is included in the second lens unit 120. For example, the area of the target range may be larger than the area of an emitting surface of the first lens unit 110. For example, the area of the target range may be smaller than or equal to an incident surface of the second lens unit 120. In addition, all light incident on the target range Tr may be incident on the pattern unit 130 through the second lens unit 120.

On the other hand, the incident angle of the light incident through the aperture Ap may be determined according to the target range Tr. Generally, an angle at which light may be incident to form an image through an aperture in a camera is defined as an angle of view, and the angle of view may be determined by the characteristics of lenses included in the camera. Like the definition of the angle of view of such a camera, the angle of view may be defined as an angle at which light may be incident on the target range Tr even in the curved pattern marker 100 of the present embodiment. For example, in the curved pattern marker 100 of FIG. 2, the angle of view A of is indicated by both arrows on the curve.

The first lens unit 110 may include only one lens or may include two or more lenses. An incident light Pin passing through the aperture to be parallel to the optical axis may be incident perpendicularly to an incident surface of the first lens unit 110. In an embodiment, the incident surface of the first lens unit 110 may be a plane. In an embodiment, the incident surface of the first lens unit 110 may be plane, which is parallel to an opening plane of the aperture Ap. In one embodiment, an area of the emitting surface of the first lens unit 110 may be larger than the area of the incident surface of the first lens unit 110.

In one embodiment, when the first lens unit 110 includes two or more lenses, the first lens unit 110 may have a structure in which the lenses are sequentially coupled with each other. For example, when the first lens unit 110 includes three lenses, the lenses may be coupled in such a manner that, in the direction in which the incident light Pin advances, an incident surface of the second lens is coupled to an emitting surface of the first lens and an incident surface of the third lens is coupled to an emitting surface of the second lens. At this time, the incident light Pin, which passes through the aperture parallel to the optical axis, may be incident perpendicularly on the incident surface of the first lens. In addition, the incident surface of the first lens may be a plane. Furthermore, an area of the emitting surface of the third lens may be larger than an area of the incident surface of the first lens. The structure of the first lens unit 110 will be described in more detail in the description of FIGS. 3 to 5.

The second lens unit 120 may include at least one lens, may receive the light emitted from the first lens unit 110, and may cause the light to be perpendicularly incident on the pattern unit 130. Here, as can be seen from FIG. 3, perpendicular incidence means that a light component passing through the center of the aperture Ap is perpendicularly incident on the pattern unit 130. This concept of perpendicular incidence may be substantially the same as the concept that light is incident on the pattern unit 130 such that the light is focused. For reference, a light component that has deviated from the center of the aperture Ap may be incident on the pattern unit 130 at an acute angle and may be reflected according to the law of reflection. For example, the second lens unit 120 may include a curved lens adjacent to the pattern unit 130, and the light incident on the second lens unit 120 may pass through an emitting surface of the curved lens and may be perpendicularly incident on the pattern unit 130. As light is perpendicularly incident on the pattern unit 130 through the second lens unit 120, the light may be perpendicularly reflected again at the pattern unit 130 and may be emitted through the second lens unit 120 and the first lens unit 110 to be parallel to the incident light Pin.

The second lens unit 120 may also include two or more lenses. When the second lens unit 120 includes two or more lenses, the lens unit may have a structure in which the lenses are sequentially coupled with each other. The structure of the second lens unit 120 will be described in more detail in the description of FIGS. 3 to 5.

The pattern unit 130 may have a concavely curved shape with respect to a plane perpendicular to the incident light Pin as illustrated in the drawings. Here, the curved surface may be, for example, spherical or paraboloid. Although not illustrated, curved patterns (see Psph in FIG. 10A) and a reflective layer (see 136 in FIG. 11A) may be formed in the pattern unit 130. The light incident on the pattern unit 130 may be reflected through the reflective layer. Since the pattern unit 130 has curved patterns, the curved patterns may be reflected in the reflected light. For example, when each of the curved patterns includes a transparent portion and an opaque portion, the light reflected by the pattern unit 130 may have different light intensities corresponding to the transparent portions and the opaque portions of the curved patterns. The structure of the pattern unit 130 will be described in more detail in the description of FIGS. 10A to 10B.

For reference, when the parallel light passes through the lens and forms an image at a point, the point may correspond to the focus of the lens. This may also be interpreted such that light emerging from the focal point passes through the lens and is emitted as the parallel light. Generally, in the case of a curved lens, only a light near the optical axis forms an image as one point at the focal point, and when a light is distant from the optical axis or has an inclination with respect to the optical axis, a spherical aberration is generated without forming an image at one point. In addition to the spherical aberration, a comatic aberration, an astigmatic aberration, a field curvature aberration, and a distortion aberration may also occur. Therefore, in the case of an existing marker comprising a curved lens and flat patterns, a distortion due to various aberrations, particularly a distortion due to a field curvature aberration, may occur in outer portions other than the central portion of the flat pattern corresponding to the focus. Therefore, in order to eliminate such distortion, lenses having various shapes and refractive indices are combined in a complicated manner such that light is incident so as to focus at all the positions of the flat patterns.

On the other hand, in the case of the curved pattern marker 100 of the present embodiment, since the curved patterns are used, light may be incident so as to be focused at all the positions of the curved patterns through a simpler combination of lenses. The curved pattern marker 100 of the present disclosure reversely uses a field curvature aberration. More specifically, although the field curvature aberration is a disadvantage in an optical system, the curved pattern marker 100 of the present disclosure reversely uses the field curvature aberration so as to make curved pattern surfaces coincide with curved focal planes. Accordingly, the incident light is focused on the pattern surfaces, which are the focal planes, so that the field curvature aberration may be automatically removed.

As a result, in the curved pattern marker 100 of the present embodiment, the pattern unit 130 is formed in a curved shape such that the pattern unit 130 is aligned with the focal planes of the lens unit, particularly, the second lens unit 120, so that various aberrations, in particular, the field curvature aberration may be effectively removed. In other words, in the curved pattern marker 100 of the present embodiment, by configuring the lens unit such with regard to the pattern unit 130 having a curved surface of a predetermined shape so that the focal plane of the lens unit, in particular the focal plane of the second lens unit, coincides with the curved surface of the pattern unit 130, the spherical aberration may be effectively removed.

Meanwhile, in the case of the curved pattern marker 100 of the present embodiment, since the curved pattern unit has a structure in which all the light is incident on the curved patterns so as to be focused, the curved pattern portions may correspond to the focal points of a virtual objective lens, which comprises the first lens unit 110 and the second lens unit 120. As described above, the light reflected from the focal planes of the lens may be emitted as parallel light through the lens. Therefore, the curved patterns of the curved pattern marker 100 of the present embodiment may, by the light reflected from the focal planes, be emitted in the form of parallel light through the first lens unit 110 and the second lens unit 120. Meanwhile, the curved patterns have a curved shape in the pattern unit 130, but the curved patterns reflected in the light through reflection may have a two-dimensional shape of a curved surface.

A process of tracking a position using the curved pattern marker 100 of the present embodiment will be briefly described. First, the curved pattern marker 100 may emit curved patterns of the pattern unit 130 in the form of parallel light through the reflection of light, the images of the curved patterns emitted in the form of parallel light may be formed as enlarged pattern images at the image-forming unit (see 500 in FIG. 13), and the position and orientation of the curved pattern marker 100 may be calculated by analyzing the pattern images by a processor (see 600 in FIG. 13). A position and orientation calculation method of a marker using a planar pattern is disclosed in Korean Patent Application No. 10-2016-0101377 (entitled "Optical Tracking Marker, Optical Tracking System, and Optical Tracking Method"), which is not published and incorporated in the present disclosure, and the same position and orientation calculation method may also be applied to the curved pattern marker 100 of the present embodiment.

In the curved pattern marker 100 of the present embodiment curved patterns of the first lens unit 110, the second lens unit 120, and the pattern unit 130 may be formed so that the curved pattern marker constitutes an infinite optical system in an optical tracking device. Accordingly, the reflected light in which the curved patterns are reflected may be emitted in the form of parallel light through the second lens unit 120 and the first lens unit 110. As described above, in the curved pattern marker 100 of the present embodiment, the curved pattern portions may correspond to the focal planes of the curved surface of the virtual objective lens comprising the first lens unit 110 and the second lens unit 120. In addition, an image-forming optical system of the optical tracking device may also comprise an infinite optical system. For example, an image sensor may be disposed at a focal position of an image-forming optical system such that parallel light incident from an infinite distance may form an image on the image sensor.

Meanwhile, the curved pattern marker 100 of the present embodiment may not comprise an infinite optical system in the optical tracking device. For example, when the optical tracking device including the curved pattern marker 100 is installed in a narrow space, even if the light emitted from the curved pattern marker 100 slightly spreads, the image-forming optical system is configured to be relatively large so as to receive most of the light emitted from the curved pattern marker 100, whereby the position and orientation of the curved pattern marker 100 can be detected relatively accurately.

The curved pattern marker 100 of the present embodiment includes the first lens unit 110, the second lens unit 120, and the pattern unit 130 having curved patterns, whereby the curved patterns may be emitted in the form of parallel light through the reflection of light. The curved pattern marker 100 of the present embodiment may obtain an image of the curved patterns using light that is incident to be focused on and reflected from the curved patterns of the pattern unit 130. In addition, when the pattern unit 130 is bonded to and disposed at the outermost curved lens of the second lens unit 120, a separate physical device for arranging the curved patterns may be unnecessary. Furthermore, when the curved patterns are used, the size of the lenses disposed at the front stage of the curved patterns may be reduced. Meanwhile, when the light is incident directly through the aperture Ap, the position of the entrance pupil relative to the angle of view may remain constant so as to prevent a position detection error of the marker from occurring. In addition, a very wide angle of view may be maintained without using a fish-eye lens, a wide-angle lens, or the like. Therefore, the curved pattern marker 100 of the present embodiment may realize a marker capable of improving the precision of position detection and orientation detection while minimizing the size.

Figure 3:
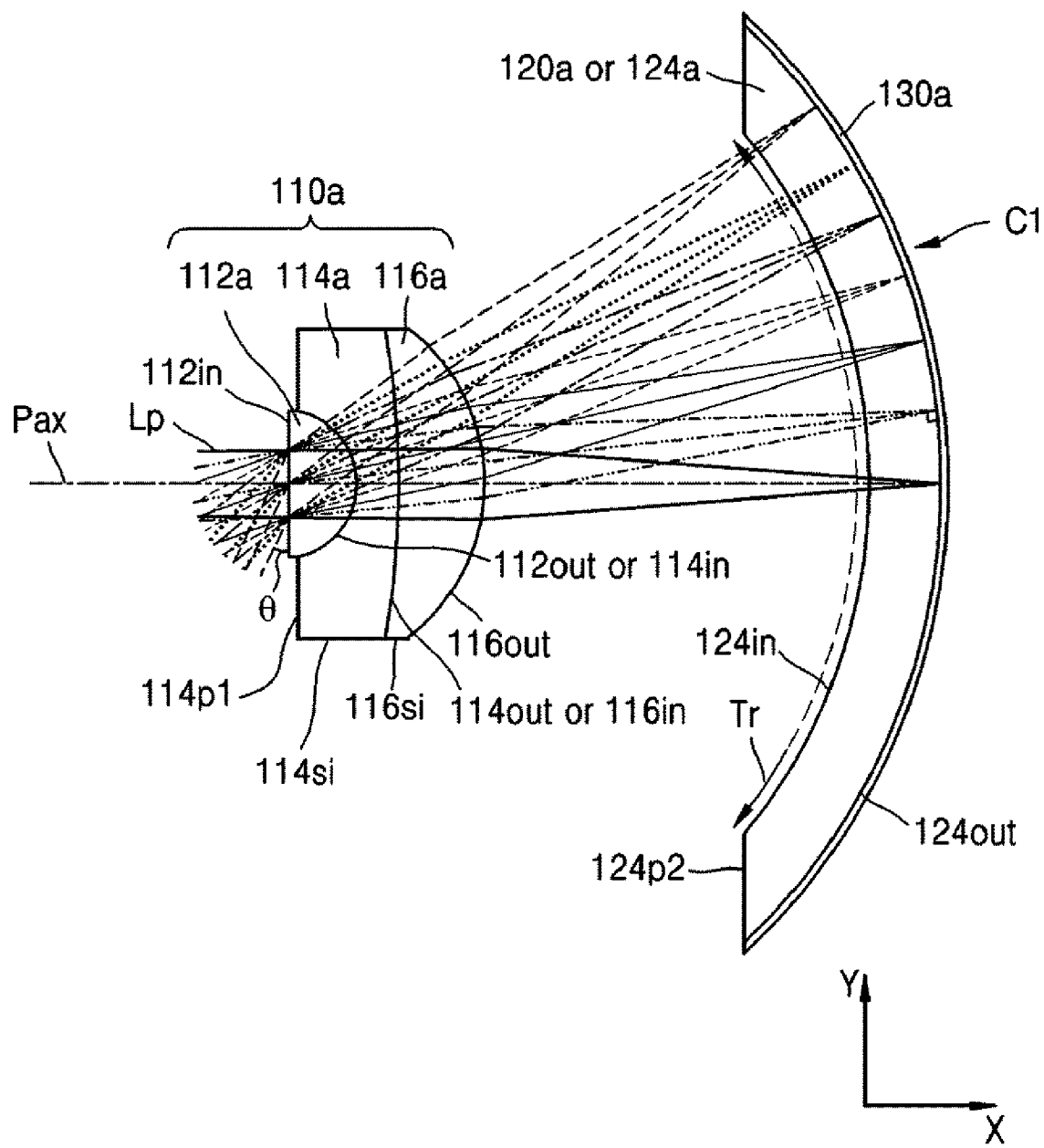
FIGS. 3 to 5 are cross-sectional views illustrating various structures of the curved pattern marker of FIG. 2 in detail.
Figure 4:
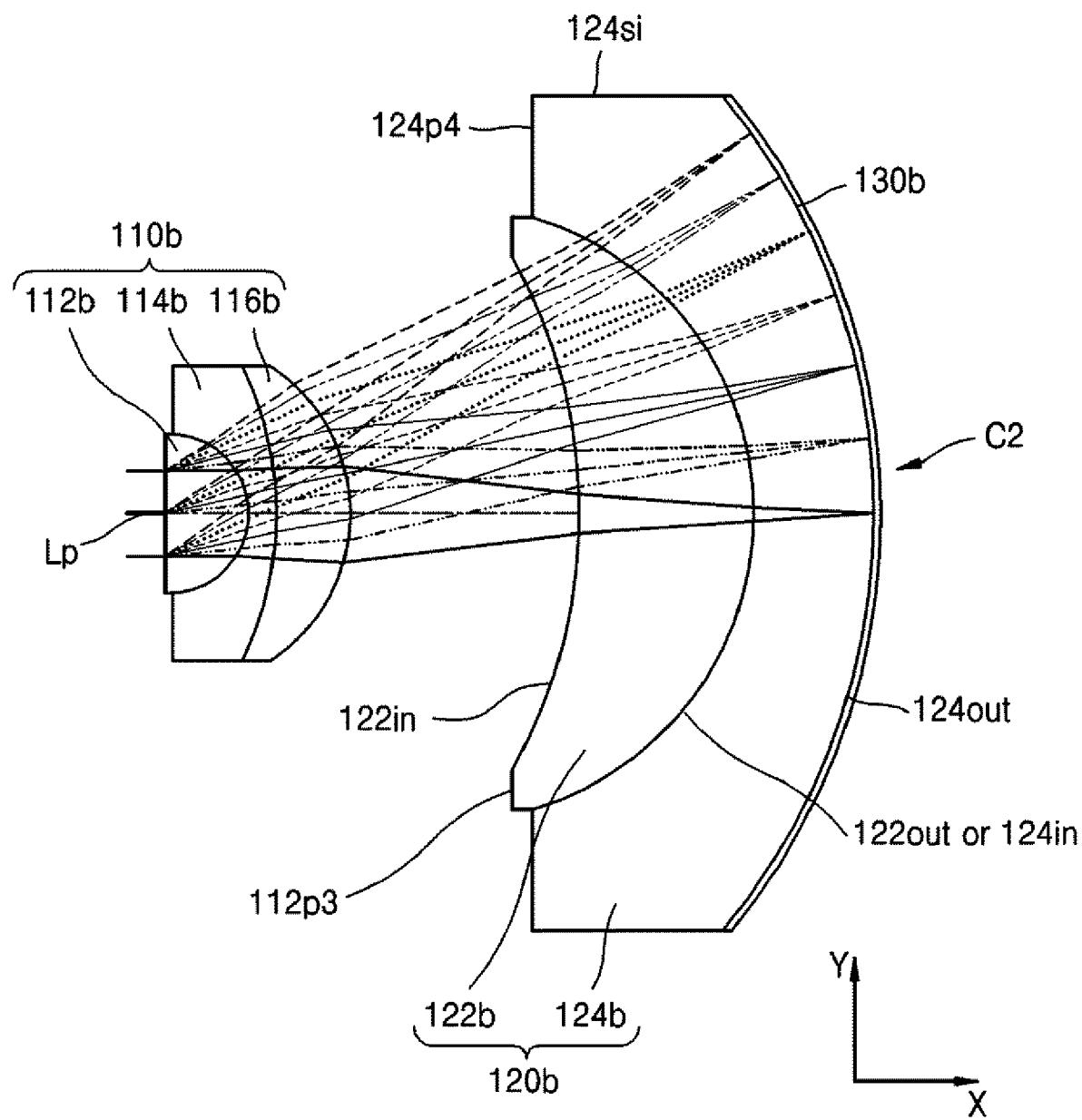
Figure 5:
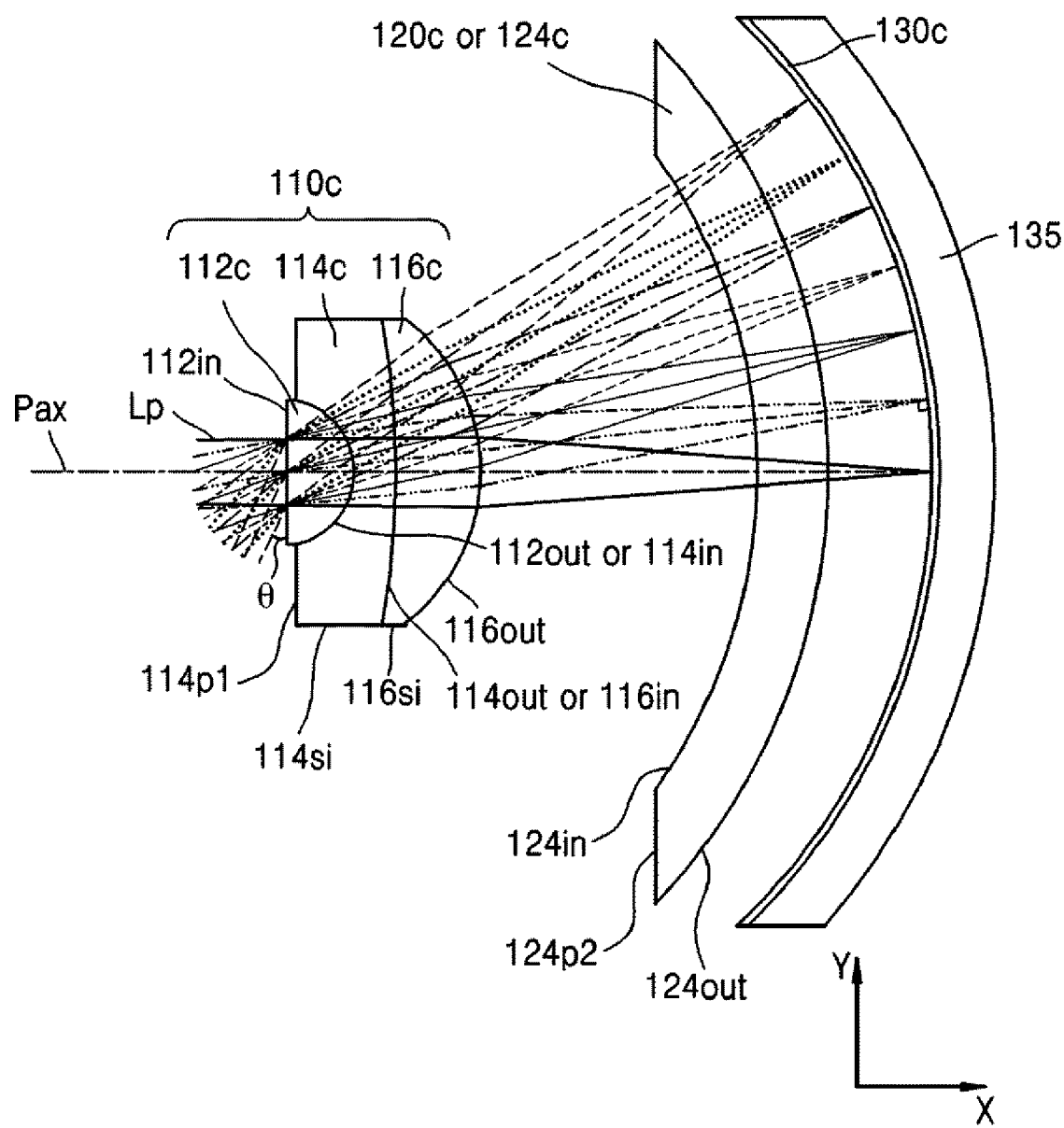

FIGS. 3 to 5 are cross-sectional views illustrating various structures of the curved pattern marker of FIG. 2 in detail.

The contents already described in the description of FIG. 2 will be briefly described or omitted.

Referring to FIG. 3, a curved pattern marker 100a of the present embodiment may include a first lens unit 110a, a second lens unit 120a, and a pattern unit 130a. As illustrated, the first lens unit 110a may include a first lens 112a, a second lens 114a, and a third lens 116a. The first lens 112a, the second lens 114a, and the third lens 116a may be sequentially coupled to each other in a first direction (X-direction) in which light is incident.

The first lens 112a has an incident surface 112in and an emitting surface 112out and may, as a whole, have the form of a spherical cap or hemisphere. That is, the incident surface 112in of the first lens 112a has a planar shape, and the emitting surface 112out may have a hemispheric shape. Meanwhile, an aperture (Ap in FIG. 2) may be defined at the incident surface 112in of the first lens 112a. For example, light may be blocked from being incident on the outer portion of the first lens 112a through the aperture.

A dot-dashed line Pax at the center corresponds to the optical axis of the lenses, and solid black lines may correspond to the parallel light Lp that is parallel to the optical axis. The aperture may limit the amount of light to such an extent that only the size of first parallel light Lp is being incident on the incident surface 112in of the first lens 112a.

The second lens 114a may include an incident surface 114in, a first plane 114p1, an emitting surface 114out, and a first side surface 114si. The second lens 114a may have a cylindrical shape as a whole, and a hemispherical groove may be formed at a portion corresponding to the first lens 112a. For example, the second lens 114a may be a negative meniscus lens or a concave meniscus lens, in which the curvature of the concave surface is greater than the curvature of the convex surface, and the concave surface may correspond to the hemispherical groove.

The incident surface 114in may have the same shape as the emitting surface 112out of the first lens 112a. Therefore, the emitting surface 112out of the first lens 112a and the incident surface 114in may have substantially the same curvature. The first plane 114p1 may be parallel to the incident surface 112in of the first lens 112a. The first plane 114p1 and the incident surface 112in of the first lens 112a may be coplanar or may have a slight step as illustrated. The emitting surface 114out may have a slightly convex structure in the first direction (X-direction). The first side surface 114si may connect the first plane 114p1 and the emitting surface 114out so as to form a cylindrical side surface.

The third lens 116a may include an incident surface 116in, an emitting surface 116out, and a second side surface 116si. The incident surface 116in may have the same shape as the emitting surface 114out of the second lens 114a. Therefore, the incident surface 116in and the emitting surface 114out of the second lens 114a may have substantially the same curvature. The emitting surface 116out may have a convex structure in the first direction (X-direction). The second side surface 116si may connect the incident surface 116in and the emitting surface 116out. In some cases, the second side surface 116si may be omitted, and the emitting surface 116out may be directly connected to the incident surface 116in. For example, the third lens 116a may be a positive meniscus lens or a convex meniscus lens, and the curvature of the concave surface may be smaller than the curvature of the convex surface. That is, the curvature of the incident surface 116in may be smaller than the curvature of the emitting surface 116out.

In the first lens unit 110a, the second lens 114a and the third lens 116a are coupled and disposed on the emitting surface 112out of the first lens 112a, whereby the spherical aberration of the first lens 112a may be reduced. In addition, the first lens unit 110a may cause the light incident on the incident surface 112in of the first lens 112a to be emitted within a target range Tr of the second lens unit 120a. Therefore, light incident at an angle smaller than a first angle θ with respect to the incident surface 112in of the first lens 112a may not be input to the second lens unit 120a. In the same sense, light emitted from the second lens unit 120a in the opposite direction to the first direction (X-direction) is emitted in the form of parallel light through the first lens unit 110a, and at an angle larger than the first angle θ with respect to the incident surface 112in of the first lens 112a. Meanwhile, when the angle of view of the curved pattern marker 100a of the present embodiment is represented by the first angle θ, the angle of view of the curved pattern marker 100a may be 2*(π/2−θ).

The second lens unit 120a may include one curved lens 124a. Therefore, in the curved pattern marker 100a of the present embodiment, the second lens unit 120a may be referred to as a curved lens 124a. The curved lens 124a may have, for example, a negative meniscus lens structure. However, as illustrated in the drawing, since the central portion and the outer portion are formed to have substantially the same thickness, there is little difference in curvature therebetween when the thickness is thin. The curved lens 124a may include an incident surface 124in, an emitting surface 124out, and a second plane 124p2. The light emitted from the first lens unit 110a may be incident on the incident surface 124in of the curved lens 124a. The target range Tr may be included within the incident surface 124in of the curved lens 124a. The light may be incident on the emitting surface 124out of the curved lens 124a such that the light is focused thereon. This may result from the fact that the pattern unit 130a is directly attached to the emitting surface 124out of the curved lens 124a as illustrated in drawing. However, when the pattern unit 130a corresponds to a composite focal plane of the first lens unit 110a and the second lens unit 120a, the pattern unit 130a may be disposed apart from the curved lens 124a. This will be described in more detail in the description of FIG. 5.

The second plane 124p2 may connect the incident surface 124in and the emitting surface 124out. The second plane 124p2 may be or may not be parallel to the incident surface 112in of the first lens 112a.

The pattern unit 130a includes a curved pattern and may be disposed by being bonded to the emitting surface 124out of the curved lens 124a with a first curvature C1. Here, the first curvature C1 may mean the curvature of a circle or the curvature of an ellipse. Because the pattern unit 130a is bonded to the emitting surface 124out of the curved lens 124a, the emitting surface 124out of the curved lens 124a may have the first curvature C1, which is substantially equal to the curvature of the pattern unit 130a. Here, the curvature of the pattern unit 130a means the curvature of the inner surface, but since the thickness of the pattern unit 130a is very thin, it may be of no practical significance to distinguish between the inner surface and the outer surface.

Referring to FIG. 4, the curved pattern marker 100b of the present embodiment may be greatly different from the curved pattern marker 100a of FIG. 3 in the structure of the second lens unit 120b. For example, in the curved pattern marker 100b of the present embodiment, the second lens unit 120b may have a structure in which two lenses are coupled. For example, the second lens unit 120b may include a fourth lens 122b having a positive (or convex) meniscus lens structure disposed on the first lens unit 110b side and a curved lens 124b having a negative (or concave) meniscus lens structure to which the pattern unit 130b is bonded. In the curved pattern marker 100b of the present embodiment, since the second lens unit 120b includes two lenses, the light may be more accurately focused on the pattern unit 130b.

When describing the second lens unit 120b of the curved pattern marker 100b of the present embodiment in more detail, the fourth lens 122b may include an incident surface 122in, an emitting surface 122out, and a third plane 122p3. The incident surface 122in is a surface to which light emitted from the first lens unit 110b is input. The incident surface 122in may include a target range and may have a slightly convex shape in a first direction (X-direction) in which light travels. The emitting surface 122out may have a hemispheric shape convex in the direction in which the light travels, and may have a curvature larger than that of the incident surface 122in. For example, the second lens unit 120b may have a positive meniscus lens structure. The third plane 122p3 connects the incident surface 122in and the emitting surface 122out and may be parallel to the incident surface of the first lens 122b. On the other hand, since a side surface exists between the emitting surface 122out and the third plane 122p3, the incident surface 122in and the emitting surface 122out may be connected to the third plane 122p3 through the side surface.

The curved lens 124b may include an incident surface 124in, an emitting surface 124out, a fourth plane 124p4, and a third side surface 124si. The incident surface 124in may be coupled to the emitting surface 122out of the fourth lens 122b with the substantially same shape. Accordingly, the incident surface 124in may have substantially the same curvature as the emitting surface 122out of the fourth lens 122b. Light may be incident on the emitting surface 124out through the incident surface 124in and may further be incident on the pattern unit 130b bonded to the emitting surface 124out to be focused thereon.

The fourth plane 124p4 may extend from the incident surface 124in and may be parallel to the third plane 122p3 of the fourth lens 122b. The fourth plane 124p4 may be coplanar with the third plane 122p3 of the fourth lens 122b and/or may have a slight step as illustrated in the drawing. The side surface 124si may connect the fourth plane 124p4 and the emitting surface 124out.

The pattern unit 130b may include a curved pattern and may be disposed by being bonded to the emitting surface 124out of the curved lens 124b with a second curvature C2. The second curvature C2 may also mean the curvature of a circle or the curvature of an ellipse. Because the pattern unit 130b is bonded to the emitting surface 124out of the curved lens 124b, the emitting surface 124out of the curved lens 124b may also have the second curvature C2, which is substantially equal to the curvature of the pattern unit 130b.

Meanwhile, the structure of the first lens unit 110b may have a structure similar to that of the first lens unit 110a of the curved pattern marker 100a of FIG. 3. For example, the first lens unit 110b may include a first lens 112b, a second lens 114b, and a third lens 116b, and each of the first lens 112b, the second lens 114b, and the third lens 116b may have a structure similar to the first lens 112a, the second lens 114a, and the third lens 116a of the curved pattern marker 100a of FIG. 3. However, strictly speaking, because the target range is changed by changing the structure of the second lens unit 120b, the structure of each of the first lens 112b, the second lens 114b, and the third lens 116b may be slightly different from the first lens 112a, the second lens 114a, and the third lens 116a of the curved pattern marker 100a of FIG. 3. For example, as illustrated, the emitting surface of the second lens 114b and the incident surface of the third lens 116b may be coupled to each other with a larger curvature than that of the curved pattern marker 100a of FIG. 3.

Meanwhile, by changing the structures of the lenses in the lens unit, the curvature, size, etc. of the pattern unit may be adjusted. Therefore, curved pattern markers provided with pattern units of various curvatures and sizes may be realized through the structure change of the lenses in the lens units. In addition, the lenses in the lens units may contribute to the adjustment of the curvature or size of the pattern unit through the adjustment of the refractive indexes in addition to structural changes.

Meanwhile, in the curved pattern markers of various embodiments, including the curved pattern marker 100b of the present embodiment, a plurality of lenses are grouped, and the advantages and roles thereof are as follows.

First, when the lenses constituting the optical systems of a curved pattern marker are grouped like the first lens unit 110b and the second lens unit 110b, the design of the optical system may be simplified. The lenses have respective aberrations, and the aberration of a lens group may be determined by summing up the aberrations of the lenses. For example, the aberration of the first lens unit 110b may be determined by summing up the respective aberrations of the first lens 112b, the second lens 114b, and the third lens 116b. The first lens unit 110b may serve to determine a focal plane or to form an overall optical path, and the second lens unit 120b may serve to compensate the distortion or chromatic aberration of the first lens unit 110b. For example, when the chromatic aberration has a positive (+) value in the first lens unit 110b, the chromatic aberration of the portion 120b may be designed to have a negative (−) value such that the sum of the chromatic aberration of the first lens unit 110b and the chromatic aberration of the second lens unit 120b is close to 0.

Meanwhile, the spherical pattern marker 100b of the present embodiment is configured such that lenses are bonded together so as to form each of the first lens unit 110b and the second lens unit 120b, and the position of the lenses may be determined close to designed values compared with a general stacked structure in which a lens group comprises lenses, which are spaced apart from each other. In addition, since the optical system is formed using bonded lenses, it is possible to improve the yield as well as to minimize the overall design deviation of curved pattern markers including the first and second lens units 110b and 120b.

Referring to FIG. 5, the spherical pattern marker 100c of the present embodiment may be different from the embodiment of FIG. 3 in that the pattern unit 130c is disposed apart from the second lens unit 120c. The basic configuration of the first lens unit 110c and the second lens unit 120c may be substantially the same as those of the first lens unit 110a and the second lens unit 120a of FIG. 3, respectively. However, the focal position of the second lens unit 120c is not in the emitting surface 124out of the curved lens 124c, but in the pattern unit 130c. Accordingly, the structure, the refractive index, and the like of the second lens unit 120c, that is, the curved lens 124c may be different from those in the embodiment of FIG. 3.

The pattern unit 130c may be disposed by being bonded to the inner surface of a support member 135 as illustrated in the drawing. The support member 135 may be disposed inside a housing that is designed to be spaced apart from the second lens unit 120c by a predetermined distance. On the other hand, the pattern unit 130c may be disposed without a separate supporting member. For example, as illustrated in FIG. 9B, the pattern unit 130c may be disposed by being bonded to the inner surface of the holder without a separate support member.

Of course, the structure in which the pattern unit is disposed apart from the second lens unit may equally be applied to the embodiment of FIG. 4 or the other embodiments described below.

Although the structures of the first lens units 110a, 110b, and 110c and the second lens units 120a, 120b, and 120c of the curved pattern markers 100a, 100b, and 100c of the present embodiment have been described, the structures of the first lens unit and the second lens unit are not limited thereto. For example, the first lens unit may have a structure including a single lens or may have a structure in which two lenses are coupled to each other. In some cases, the first lens unit may have a structure in which four or more lenses are coupled to each other. The second lens unit may also have a structure in which three or more lenses are coupled to each other. Meanwhile, the structure of each of the lenses constituting the first lens unit and the structure of each of the lenses constituting the second lens unit may be variously changed depending on the curvature and the size of the pattern unit. In addition, the refractive index of each of the lenses of the first lens unit and the refractive index of each of the lenses of the second lens unit may be variously changed.

FIG. 6 is a conceptual view of a structure of a curved pattern marker according to an embodiment of the present disclosure. The contents already described in the description of FIGS. 2 to 5 will be briefly described or omitted.

Referring to FIG. 6, the curved pattern marker 200 of the present embodiment may be different from the curved pattern marker 100 of FIG. 2 in view of the fact that the curved pattern marker 200 further includes a third lens unit 240. That is, the curved pattern marker 200 of the present embodiment may include a first lens unit 210, a second lens unit 220, a pattern unit 230, and a third lens unit 240.

The third lens unit 240 may be disposed at the front stage of the aperture Ap and may include at least one lens. The third lens unit 240 may function to condense external light and input the light into the aperture Ap. For example, when light is directly incident on the aperture Ap, the angle of view is small and the light may not be sufficiently incident thereon. Further, the range of the parallel light of a curved pattern emitted through reflection may also be limited, and thus the spatial arrangement range of an image-forming unit for detecting the parallel light of the curved pattern may also be limited. However, by condensing light and causing the light to be incident on the aperture Ap using a wide-angle lens or the like, it is possible to increase the amount of light and it is also possible to widen the spatial arrangement range of the image-forming unit.

Since the curved pattern marker 200 of the present embodiment includes the third lens unit 240 disposed at the front stage of the aperture Ap, it is possible to increase the amount of light incident on the aperture Ap, and it is also possible to widen the spatial arrangement range of the image-forming unit of the optical tracking device.

Figure 7A:
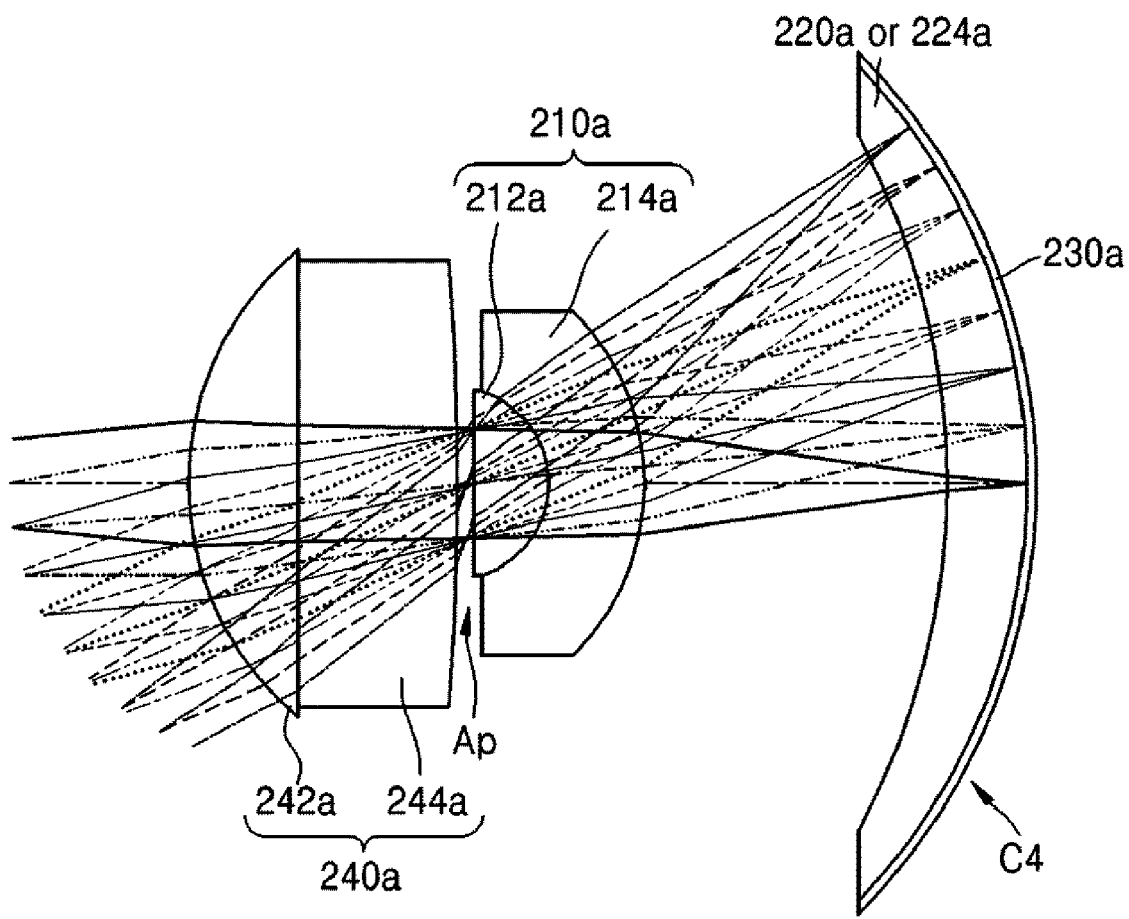
FIGS. 7A and 7B are cross-sectional views illustrating various structures of the curved pattern marker of FIG. 6 in detail.
Figure 7B:
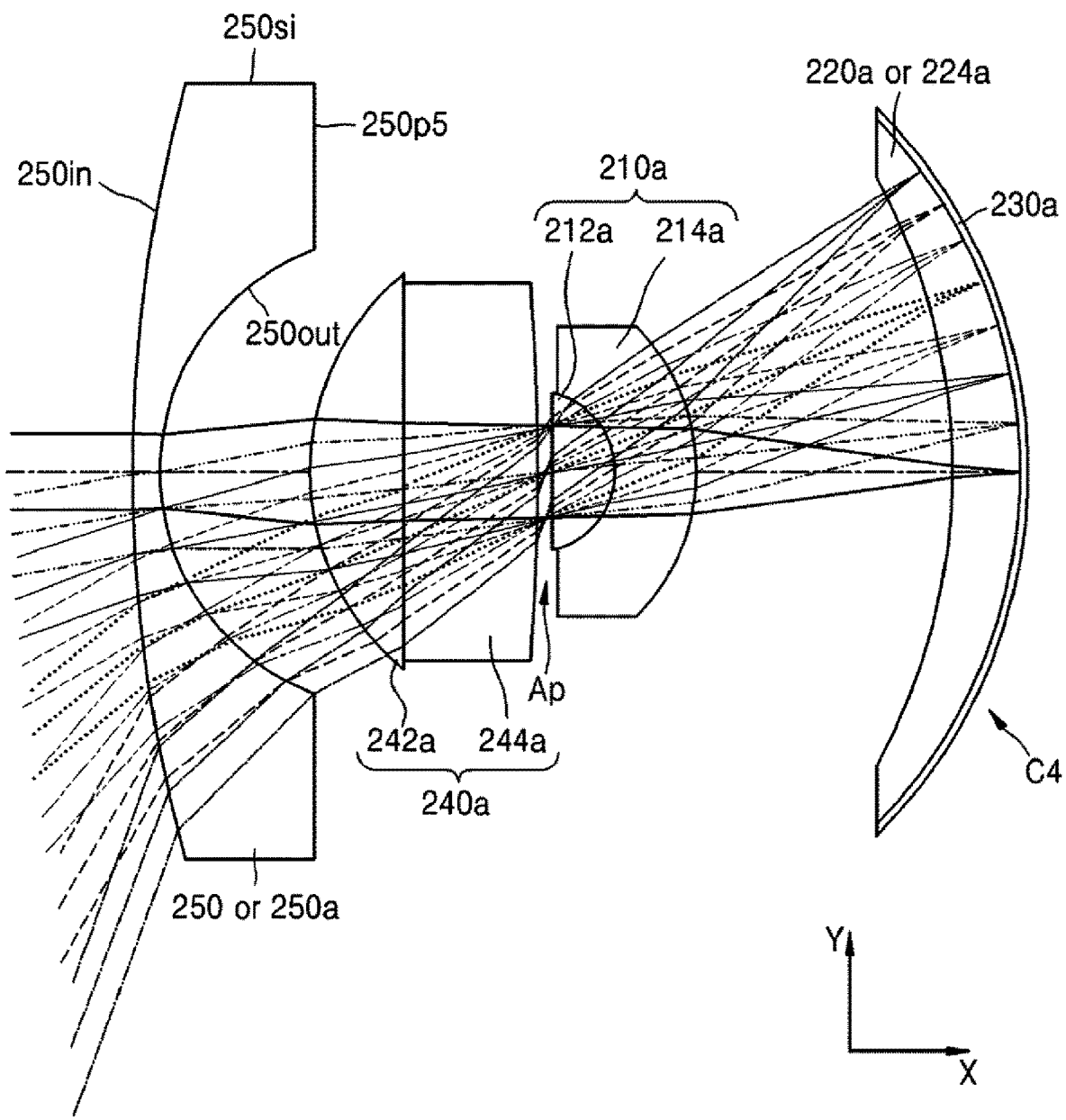

FIGS. 7A and 7B are cross-sectional views illustrating various structures of the curved pattern marker of FIG. 6. The contents already described in the description of FIGS. 2 to 6 will be briefly described or omitted.

Referring to FIG. 7A, a curved pattern marker 200a of the present embodiment may include a first lens unit 210a, a second lens unit 220a, a pattern unit 230a, and a third lens unit 240a. The first lens unit 210a, the second lens unit 220a, and the pattern unit 230a are similar to the first lens unit 110a, the second lens unit 120a, and the pattern unit 130a, but may slightly differ from the first lens unit 110a, the second lens unit 120a, and the pattern unit 130a in the specific structures of FIG. 3.

More specifically, the first lens unit 210a may include two lenses, that is, a first lens 212a and a second lens 214a. The first lens 212a may have a hemispherical shape. An aperture may be defined adjacent to the incident surface of the first lens 212a. In the second lens 214a, the side surface may have a cylindrical shape, the emitting surface may be convex in a first direction (X-direction) in which the light travels, and the incident surface may have a hemispherical groove shape to correspond to the emitting surface of the first lens 212a. For example, the second lens 214a may have a negative meniscus lens structure. As illustrated in the drawing, the incident surface of the second lens 214a may be coupled to the emitting surface of the first lens 212a so as to constitute the first lens unit 210a.

In the curved pattern marker 100a of FIG. 3, the first lens unit 110a includes three lenses, but in the curved pattern marker 200a of the present embodiment, the first lens unit 210a may include only two lenses. However, the structure of the first lens unit 210a is not limited thereto. For example, in the curved pattern marker 200a of the present embodiment, the first lens unit 210a may have a structure in which three lenses are coupled to each other.

The second lens unit 220a may be configured with one curved lens 224a. Light from the first lens unit 210a may be incident on the incident surface of the curved lens 224a and may be incident through the emitting surface of the curved lens 224a to be focused on the pattern unit 230a. The pattern unit 230a includes a curved pattern and may have a fourth curvature C4. The fourth curvature C4 may also mean the curvature of a circle or the curvature of an ellipse. The pattern unit 230a may be disposed by being bonded to the emitting surface of the curved lens 224a.

The pattern unit 230a may differ from the pattern unit 130a of the curved pattern marker 100a of FIG. 3 in curvature and size. For example, the curvature of the pattern unit 230a may be greater than the curvature of the pattern unit 130a of the curved pattern marker 100a of FIG. 3. In addition, the size of the pattern unit 230a may be smaller than the size of the pattern unit 130a of the curved pattern marker 100a of FIG. 3. However, the curvature and size of the pattern unit 230a are not limited to the above-described contents. For example, the pattern unit 230a may have substantially the same curvature and size as the pattern unit 130a of the curved pattern marker 100a of FIG. 3.

The structure of the second lens unit 220a may slightly differ from the structure of the second lens unit 120a of the curved pattern marker 100a of FIG. 3. For example, based on the difference in curvature between the pattern units 130a and 230a, the curvature of the emitting surface of the curved lens 224a may be greater than the curvature of the curved lens 124a of the curved pattern marker 100a of FIG. 3. In addition, while the curved lens 124a of the curved pattern marker 100a of FIG. 3 has a uniform thickness as a whole, the curved lens 224a of the curved pattern marker 200a of the present embodiment may have a structure in which the thickness is reduced toward the outer portion. For example, the curved lens 224a may have a positive meniscus lens structure. However, the structure of the second lens unit 220a is not limited to the above-described contents. For example, the second lens unit 220a may have substantially the same structure as the second lens unit 120a of the curved pattern marker 100a of FIG. 3. In addition, the second lens unit 220a may be a single curved lens, or may have a structure in which two or more lenses are coupled to each other as in the curved pattern markers 100b and 100c of FIGS. 4 and 5.

The third lens unit 240a may be disposed apart from the first lens unit 210a in the second direction (−X-direction) opposite to the first direction (X-direction), and may include two lenses, that is, a fifth lens 242a and a sixth lens 244a. However, the present disclosure is not limited thereto, and the third lens unit 240a may be implemented as a single lens. The third lens unit 240a may be designed to condense light, which passes through the third lens unit 240a, at the aperture Ap facing the emitting surface of the sixth lens 244a. To this end, the fifth lens 242a may have a hemispherical shape as a whole. For example, the incident surface of the fifth lens 242a may have a hemispherical shape that is convex in the second direction (−X-direction), and the emitting surface of the fifth lens 242a may have a planar shape. The sixth lens 244a may have a cylindrical structure. The incident surface of the sixth lens 244a may have a planar shape, and the emitting surface may have a shape that is slightly convex in the first direction (X-direction) but close to a plane. For example, the sixth lens 244a may have a positive meniscus lens structure. According to the embodiment, the third lens unit 240a may be implemented as a single lens in which the incident surface of the sixth lens 244a is coupled to the emitting surface of the fifth lens 242a, for example, as a cylindrical plano-convex lens or a cylindrical double convex lens.

As illustrated in the drawing, the third lens unit 240a functions to condense light and to cause the condensed light to be incident on the aperture Ap. For example, the aperture Ap is defined between the third lens unit 240a and the first lens unit 210a, or on the incident surface of the first lens 212a of the first lens unit 210a, and light is condensed at the aperture Ap through the third lens unit 240a so as to be incident on the first lens unit 210a.

Referring to FIG. 7B, a curved pattern marker 200b of the present embodiment may be different from the curved pattern marker 200a of FIG. 7A in view of the fact that the curved pattern marker 200b further includes a fourth lens unit 250. For example, the curved pattern marker 200b of the present embodiment may further include the fourth lens unit 250 disposed at the front stage of the third lens unit 240a in the second direction (−X-direction).

The fourth lens unit 250 may comprise a single lens of a seventh lens 250a, and may include an incident surface 250in, an emitting surface 250out, a fifth plane 250p5, and a fourth side surface 250si. The incident surface 250in of the seventh lens 250a has a shape slightly convex in the second direction (−X-direction), and the emitting surface 250out may have a hemispherical groove shape having a curvature, which is substantially equal to that of the incident surface of the fifth lens 242a. For example, the seventh lens 250a may have a negative meniscus lens structure. The fifth plane 250p5 may extend from the emitting surface 250out and may be parallel to the incident surface of the sixth lens 244a. The fourth side surface 250si may connect the incident surface 250in and the fifth plane 250p5.

It is possible to maximize the angle of view of the curved pattern marker 200b like a fish eye lens using the fourth lens unit 250, and thus it is possible to condense a wider range of light and to cause the condensed light to be incident on the aperture Ap. Further, the spatial arrangement range of an image-forming unit configured to detect parallel light of a curved pattern may be further increased due to the expansion of the angle of view.

In the curved pattern markers 200a and 200b illustrated in FIGS. 7A and 7B, a structure in which the third lens unit 240a is disposed at the front stage of the aperture, or a structure in which the third lens unit 240a and the fourth lens unit 250 are arranged at the front stage of the aperture is exemplified. However, the structure of the curved pattern marker of the present embodiment is not limited thereto. For example, a structure in which all the lens units are disposed at the front stage of the aperture so as to condense light and to cause the condensed light to be incident on the aperture portion may be applied to the curved pattern marker of the present embodiment.

FIG. 8 is a conceptual view of a structure of a curved pattern marker according to an embodiment of the present disclosure. The contents already described in the description of FIGS. 2 to 7B will be briefly described or omitted.

Referring to FIG. 8, a curved pattern marker 300 of the present embodiment may include a first lens unit 310 and a pattern unit 330. The curved pattern marker 300 of the present embodiment may correspond to the structure in which the second lens unit 120 is omitted from the curved pattern marker 100 of FIG. 2. Accordingly, a light incident through the first lens unit 310 may be focused on a curved pattern in the pattern unit 330.

The structure of the first lens unit 310 may include at least one lens as previously described in the other embodiments. However, unlike the other embodiments, a light emitted from the first lens unit 310 is directly incident so as to be focused on a curved pattern of the pattern unit 330, rather than being incident on the second lens unit, and thus the structures, reflective indexes, and the like of the lenses constituting the first lens unit 310 may be adjusted differently from those in the first lens unit of the other embodiments. While various structures of curved pattern markers have been exemplified and described, the technical idea of the present disclosure is not limited to the exemplified structures. For example, all curved pattern marker structures, in which one or more lens units each having a number of various lenses and a lens combination structure are provided an incident light, which is incident to be parallel to the optical axis and passes through an aperture, is caused to be perpendicularly incident on the incident surface of one lens unit, such incident light is transmitted to be focused on a curved pattern in a pattern unit, and in which the incident light may be emitted in the form of a parallel light, belong to the technical idea of the present disclosure.

Figure 9:
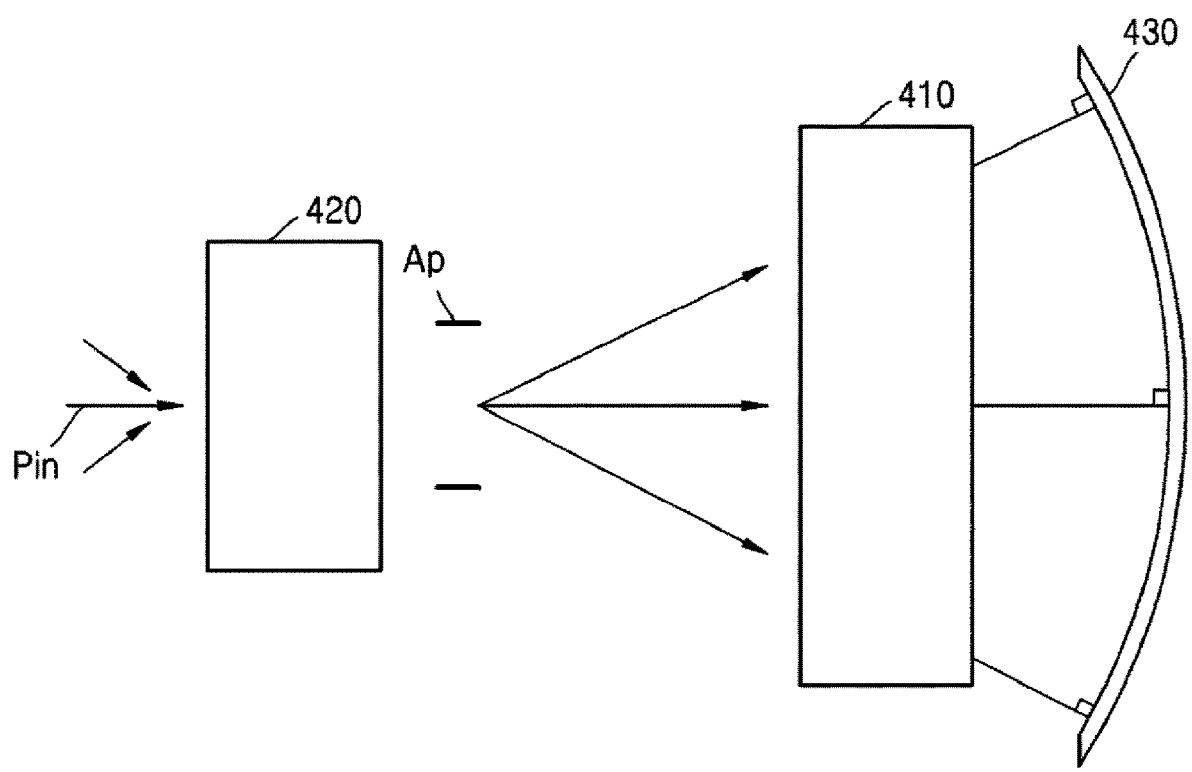
FIG. 9 is a conceptual view of a structure of a curved pattern marker according to an embodiment of the present disclosure.

FIG. 9 is a conceptual view of a structure of a curved pattern marker according to an embodiment of the present disclosure. The contents already described in the description of FIGS. 2 to 7B will be briefly described or omitted.

Referring to FIG. 9, a curved pattern marker 400 of the present embodiment may include a first lens unit 410, a second lens unit 420, and a pattern unit 430. The curved pattern marker 400 of the present embodiment may correspond to the curved pattern marker 100 of FIG. 2 in terms of construction, and may correspond to the curved pattern marker 200 of FIG. 6 in terms of function. Specifically, the curved pattern marker 400 of the present embodiment may include two lens units 410 and 420 like the curved pattern marker 100 of FIG. 2.

The aperture Ap may be disposed in front of the incident surface of the first lens unit 410 and may limit a cross-sectional area through which incident light is incident on the incident surface of the first lens unit 410. The first lens unit 410 may cause a light, which is incident through the aperture Ap, to be incident on the pattern unit 430 so as to be focused therein. All the light incident through the aperture Ap may be incident within the target range of the first lens unit 410. For example, all the light incident through the aperture Ap may be incident on the incident surface of the first lens of the first lens unit 410. In the curved pattern marker 400 of the present embodiment, the lens unit configured to emit the light, which is incident on the aperture portion, within the target range may be omitted. Thus, the first lens unit 410 may be formed in such a structure that all light incident on the aperture Ap may be emitted within the target range. When the second lens unit 420 is disposed at the front stage of the aperture Ap, the second lens unit 420 is capable of functioning to gather light incident with a wide angle of view at the aperture Ap.

Figure 10B:
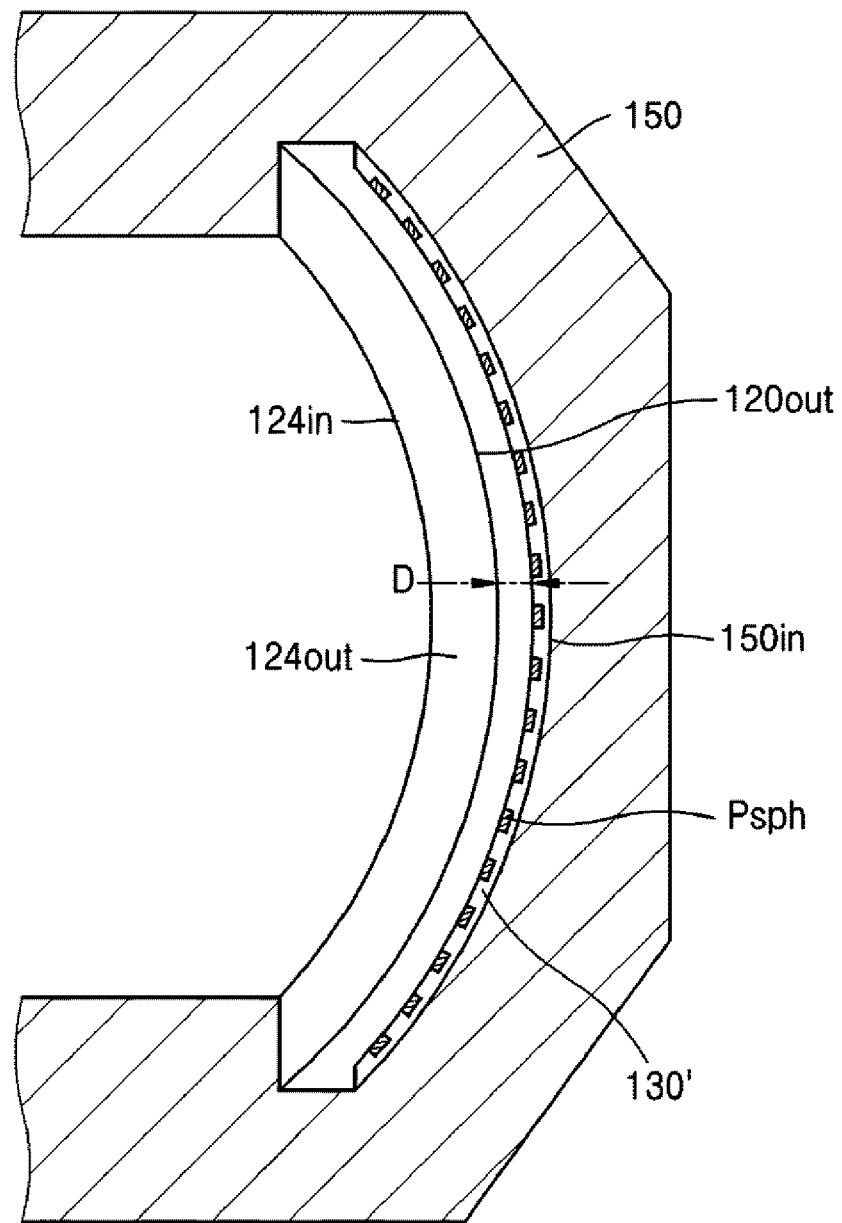

FIGS. 10A and 10B are cross-sectional views illustrating an arrangement structure of a pattern unit in curved pattern markers according to embodiments of the present disclosure.

Referring to FIG. 10A, the pattern unit 130 may include curved patterns Psph on the inner surface thereof. In the curved pattern marker of the present embodiment, the pattern unit 130 may be disposed by being bonded to the emitting surface 124out of the curved lens 124 disposed at the outermost position. Thus, light incident on the curved lens 124 may be incident on the curved patterns Psph of the pattern unit 130 through the emitting surface 124out to be focused on the curved patterns Psph.

Since the pattern unit 130 including the curved patterns Psph is bonded to the emitting surface of the curved lens 124 disposed at the outermost position, a separate physical device for arrangement of the curved patterns may be unnecessary for the curved pattern marker of the present embodiment. In addition, since the curved patterns of the pattern unit 130 are emitted as parallel light through reflection, a separate light source for emitting the curved patterns to the outside may be unnecessary for the curved pattern marker of the present embodiment. Therefore, the curved pattern marker of the present embodiment is capable of contributing to simplification and minimization of the marker structure.

Referring to FIG. 10B, in the curved pattern marker of the present embodiment, the curved lens 124 disposed at the outermost position may be accommodated and fixed in a holder 150. Generally, the lenses of the lens unit of the curved pattern marker may be accommodated in the holder 150 and may be supported and fixed by the holder 150. Thus, the inside of the holder 150 may be formed to have a structure that accommodates and supports the lenses of the lens unit, but does not disturb the travel of light.

In the curved pattern marker of the present embodiment, among the inner surfaces of the holder 150, the inner surface 150in facing the emitting surface 124out of the curved lens 124 has a curved shape, and may be disposed at a focal plane position at which a light emitted from the curved lens 124 may be focused. In the curved pattern marker of the present embodiment, the pattern unit 130' may be disposed by being bonded to the inner surface 150in of the holder 150 having the above-described structure. The pattern unit 130' may be spaced apart from the emitting surface 124out of the curved lens 124 by a first distance D. The first distance D may be very fine and less than a few millimeters. Of course, the first distance is not limited to this value. Meanwhile, as in FIG. 10A, the pattern unit 130 may be disposed by being bonded to the emitting surface 124out of the curved lens 124, and the inner surface 150in of the holder 150 may be in close contact with and cover the pattern unit 130. When the pattern unit 130 is disposed in this structure, the first distance D may be substantially close to zero. Conversely, the pattern unit 130 may be disposed by being bonded to the inner surface 150in of the holder 150, and the holder 150 may be in close contact with and cover the curved lens 124.

In the case of the structure in which the holder is in close contact with and covers the curved lens 124, the emitting surface 124out of the curved lens 124 and the inner surface 150in of the holder 150 may share the same center of curvature, and the pattern unit 130' may also share the same center of curvature as the emitting surface 124out of the curved lens 124. Therefore, a light incident from the emitting surface 124out of the curved lens 124 may be focused on the pattern unit 130'.

In the curved pattern marker, the holder 150 may be formed integrally or detachably. When the holder 150 is formed detachably and the pattern unit 130' is disposed in the holder 150, it is possible to implement a pattern-changeable curved pattern marker. As in the arrangement structure of the pattern unit 130' in the curved pattern marker of FIG. 10A, in the curved pattern marker of the present embodiment, a separate physical device for arranging the curved patterns may also be unnecessary for the arrangement structure of the pattern unit 130'. Therefore, the curved pattern marker of the present embodiment is also capable of contributing to simplification and minimization of the marker structure.

On the other hand, in the arrangement structure of the pattern units 130 and 130' of FIGS. 10A and 10B, the exemplified curved lens 124 may correspond to, for example, the curved lens 124a of the curved pattern marker 100a of FIG. 3. However, the structure of the curved lens 124 is not limited to the structure of the curved lens 124a of the curved pattern marker 100a of FIG. 3. For example, the curved lens 124 may have the structure of the curved lens 124b, 124c, and 224a disposed at the outermost position in the curved pattern markers 100b, 100c, 200a, and 200b of FIGS. 4, 5, 7A, and 7B.

Figure 11A:
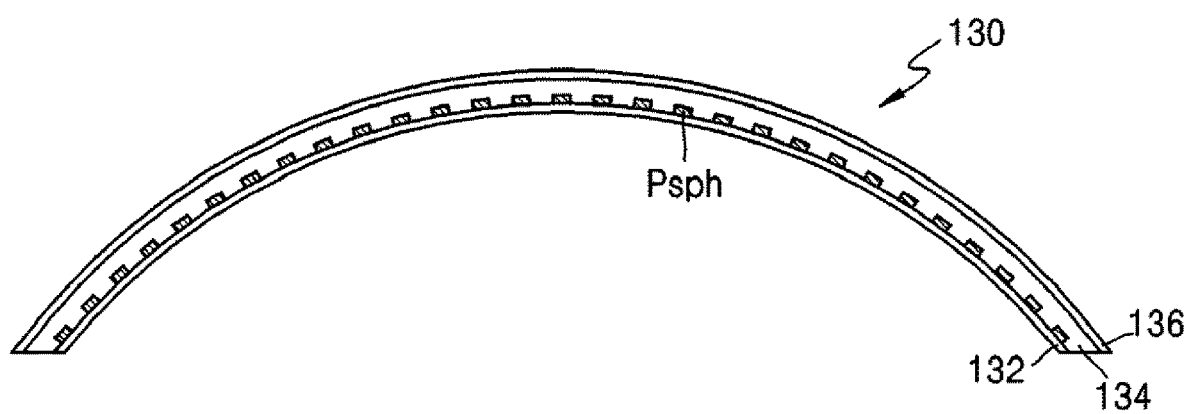
FIGS. 11A to 11C are cross-sectional views illustrating the portion of the pattern unit in a curved pattern marker according to an embodiment of the present disclosure.
Figure 11B:
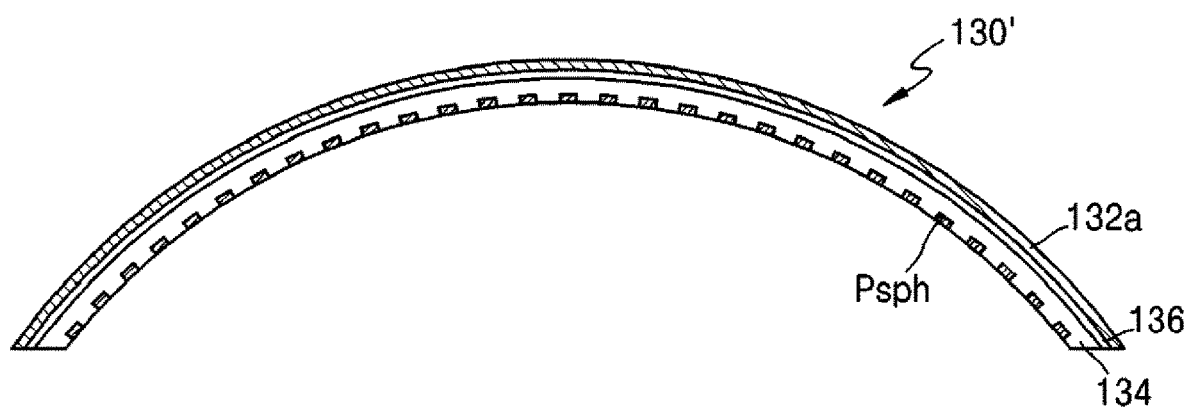
Figure 11C:
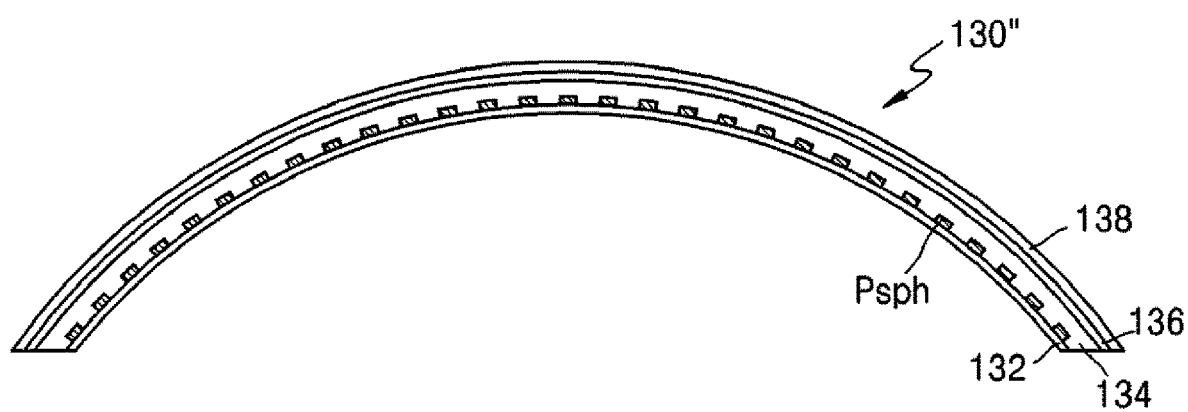

FIGS. 11A to 11C are cross-sectional views illustrating a pattern unit in a curved pattern marker according to an embodiment of the present disclosure.

Referring to FIG. 11A, in the curved pattern marker of the present embodiment, the pattern unit 130 may include an adhesive layer 132, a pattern layer 134, and a reflective layer 136. The adhesive layer 132 has a very thin thickness and is capable of bonding the pattern layer 134 to the emitting surface of the outermost curved lens (see 124a and the like in FIG. 3). The adhesive layer 132 may be formed of a transparent material capable of transmitting light.

The pattern layer 134 may include curved patterns Psph. The curved patterns Psph may be formed of an opaque material. The material constituting the pattern layer 134 other than the curved patterns Psph may be formed of a transparent material through which light may be transmitted. In general, the curved pattern may be a concept that includes both opaque and transparent portions. However, for the convenience of explanation, only the opaque portion is indicated and described as the curved pattern Psph. Hereinafter, the same concept may also be applied to the pattern units 130' and 130" illustrated in FIGS. 11B and 11C.

The reflective layer 136 may be formed thin on the outer surface of the pattern layer 134. The reflective layer 136 may be formed of a material having a high reflectance capable of reflecting light. For example, the reflective layer 136 may be formed of a metal such as aluminum, gold, or silver. Of course, the material of the reflective layer 136 is not limited to metal. Occasionally, the pattern layer 134 may be formed of a reflective material, and the reflective layer 136 may be omitted.

In general, the light used in the optical tracking device may be infrared rays. Therefore, the criterion for transparency and opacity of the adhesive layer 132, the pattern layer 134, the curved pattern Psph, and the reflective layer 136 may be infrared rays. However, the criterion for transparency and opacity of the adhesive layer 132, the pattern layer 134, the curved patterns Psph, and the reflective layer 136 is not limited to infrared rays. For example, visible rays or ultraviolet rays may also serve as the criterion for transparency and opacity.

Light, which is incident on the transparent portions of the pattern layer 134, may pass through the pattern layer 134 and may be reflected by the reflective layer 136. However, light, which is incident on the opaque portions of the pattern layer 134, i.e. the curved patterns Psph, is blocked and thus may not be reflected by the reflective layer 136. Therefore, the curved patterns Psph may be reflected in the reflected light reflected from the pattern unit 130. For example, the light intensity of the portions of the reflected light corresponding to the transparent portions of the pattern layer 134 may be high and the intensity of the portions of the reflected light corresponding to the opaque portions, i.e. the curved patterns Psph, may be low.

In FIG. 11A, the pattern unit 130 is illustrated as a curved shape. The pattern unit 130 may be attached to the emitting surface of the curved lens or the inner surface of the holder. Therefore, the pattern unit 130 before being bonded to the emitting surface of the curved lens or the inner surface of the holder may have a planar shape. Hereinafter, the same concept may also be applied to the shapes of the pattern units 130' and 130" illustrated in FIGS. 11B and 11C.

Referring to FIG. 11B, in the curved pattern marker of the present embodiment, the pattern unit 130' may include an adhesive layer 132a, a pattern layer 134, and a reflective layer 136, like the pattern unit 130 of FIG. 11A. However, in the curved pattern marker of the present embodiment, the pattern unit 130' may have a structure in which the adhesive layer 132a is formed as the outer surface of the reflective layer 136, unlike the structure of the pattern unit 130 of FIG. 11A. The pattern unit 130' may be included in the curved pattern marker as a structure bonded to the inner surface 150in of the holder 150, as illustrated in FIG. 10B. On the other hand, since the adhesive layer 132a is formed on the outer surface of the reflective layer 136, the material of the adhesive layer 132a may not be limited to a transparent material.

Referring to FIG. 11C, in the curved pattern marker of the present embodiment, the pattern unit 130" may further include a protective layer 138, unlike the pattern unit 130 of FIG. 11A. For example, in the curved pattern marker of the present embodiment, the pattern unit 130" may further include a protective layer 138 that covers the outer surface of the reflective layer 136. The protective layer 138 may protect the reflective layer 136 and the pattern layer 134 disposed inside from external physical and chemical damage. Thus, the protective layer 138 may be formed of a material that is chemically resistant and relatively hard.

Figure 12A:
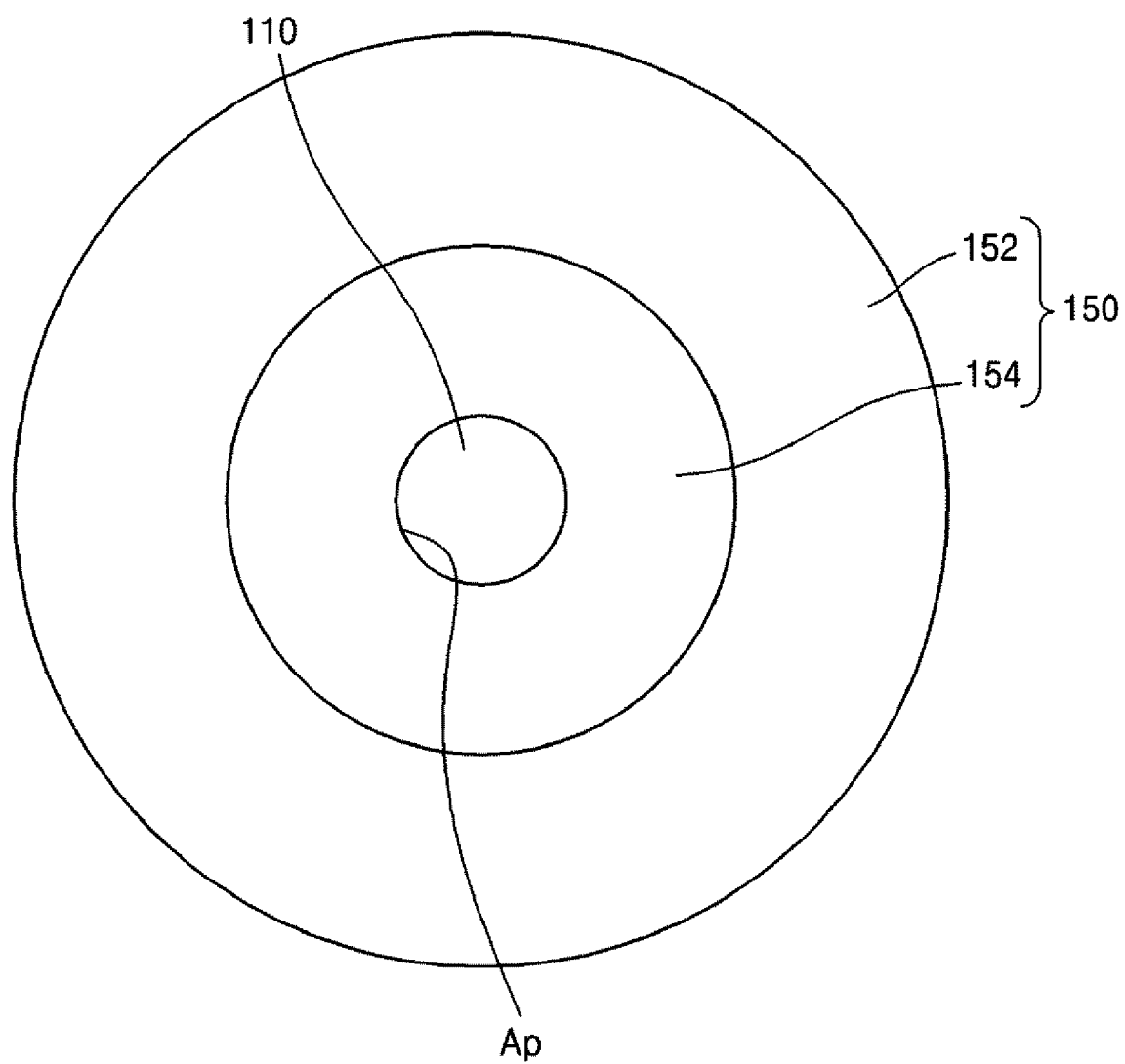
FIGS. 12A and 12B are a plan view and a side view illustrating a holder portion of a curved pattern marker according to an embodiment of the present disclosure.
Figure 12B:
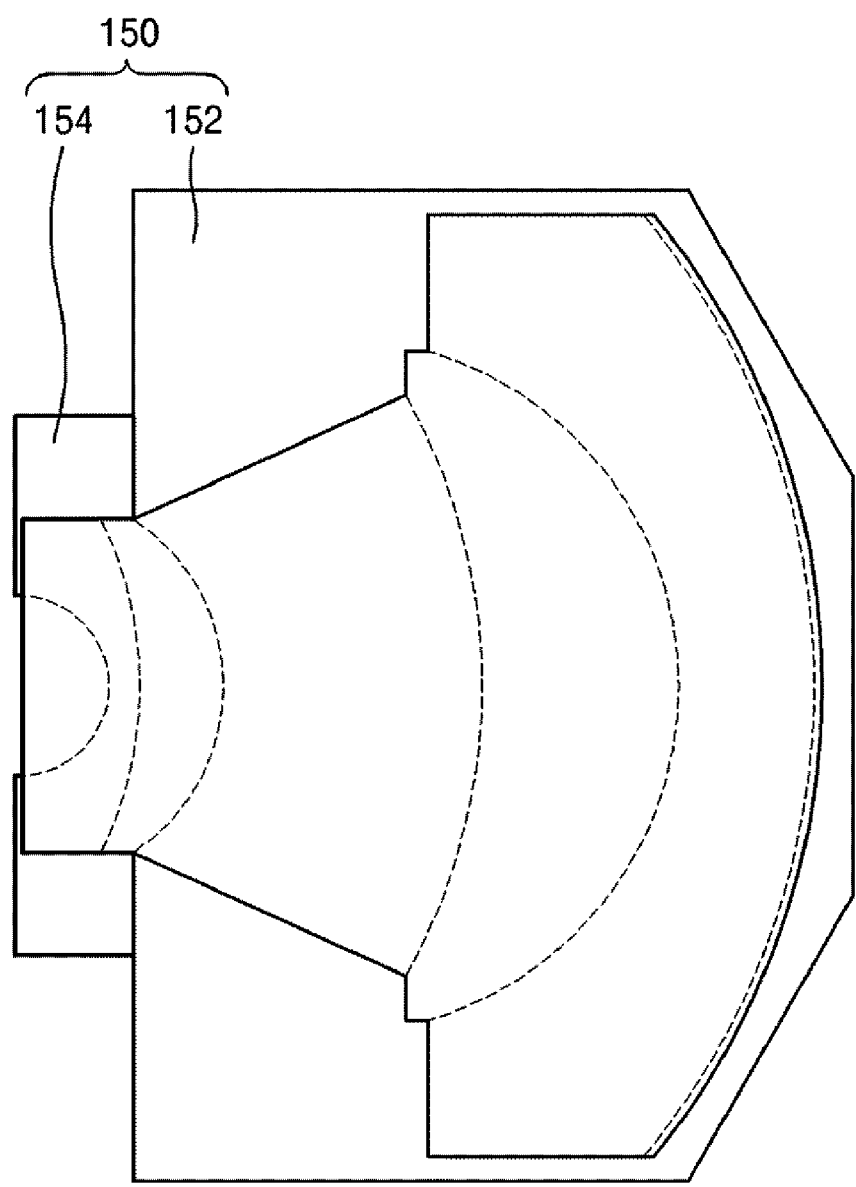

FIGS. 12A and 12B are a plan view and a side view illustrating a holder portion of a curved pattern marker according to an embodiment of the present disclosure.

Referring to FIGS. 12A and 12B, the holder 150 may include a body portion 152 and an inlet portion 154. The external appearance of the body portion 152 may have a substantially cylindrical shape. In addition, as illustrated in FIG. 12B, the cross-sectional area of the body portion 152 may decrease toward the rear surface S2 such that the area of the rear surface S2 is smaller than that of the front surface S1. However, the structure of the holder 150 is not limited thereto. For example, the holder 150 may be formed in the same shape as a general cylindrical shape in which the front surface S1 and the rear surface S2 have the same area.

The inlet portion 154 is disposed at the front surface S1 of the body portion 152 and may have a cylindrical shape. As illustrated in FIG. 12A, an opening portion corresponding to the aperture Ap may be formed in the inlet portion 154, and the lenses of the first lens unit 110 may be exposed through the open region.

Inside the holder 150, a space for accommodating and supporting the lenses of the lens units of the curved pattern marker may be provided. As indicated by dotted lines in FIG. 12B, the first lens unit 110b and the second lens unit 120b of the curved pattern marker 100b of FIG. 4 may be accommodated and supported in the holder 150. The first lens unit 110b may be disposed on the inlet portion 154 side and the second lens unit 120b may be disposed on the rear surface S2 side of the body portion 152. Although not illustrated, a pattern unit may be bonded to the emitting surface of the curved lens 124b of the second lens unit 120b or may be bonded to the inner surface of the holder 150 facing the emitting surface of the curved lens 124b. In general, since the marker includes the holder, the curved pattern marker 100b of FIG. 4 may also include the holder 150.

In the curved pattern markers of the present embodiment, the inner structure of the holder is not limited to the structure for accommodating the lens units of FIG. 4. For example, in the curved pattern markers of the present embodiment, the inner structure of the holder may have a structure capable of accommodating and supporting the lens units of FIGS. 3, 5, 7A, and 7B. Furthermore, the internal structure of the holder is not limited to the lens units of FIGS. 3, 5, 7A, and 7B, and may have a structure capable of accommodating lens units of other structures that may be included in a curved pattern marker. Meanwhile, the external appearance of the holder is not limited to the structures of FIGS. 12A and 12B, but may be formed in various shapes.

Figure 13:
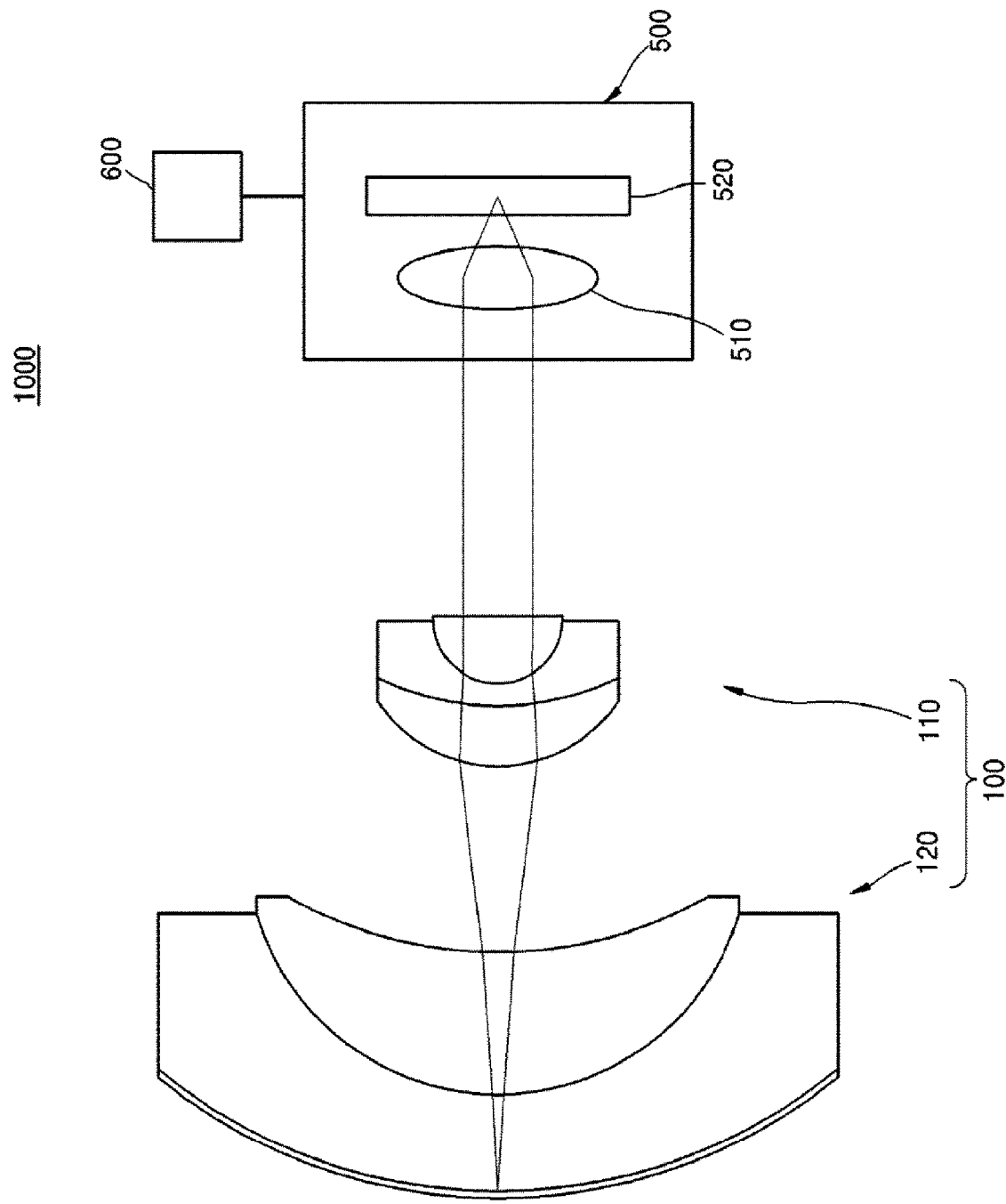
FIG. 13 is a configuration view of an optical tracking device including a curved pattern marker according to an embodiment of the present disclosure.

FIG. 13 is a configuration view of an optical tracking device including a curved pattern marker according to an embodiment of the present disclosure. The contents already described in the description of FIGS. 2 to 12B will be briefly described or omitted.

Referring to FIG. 13, an optical tracking device 1000 of the present embodiment may include a curved pattern marker 100, an image-forming unit 500, and a processor 600.

The curved pattern marker 100 is able to output curved patterns of the pattern unit 130 in the form of parallel light by reflection of light using the first lens unit 110 and the second lens unit 120. The curved pattern marker 100 may be the curved pattern marker 100b of FIG. 4. However, the structure of the curved pattern marker 100 is not limited to the structure of the curved pattern marker 100b of FIG. 4. For example, it is needless to say that the curved pattern markers 100a, 100c, 200a, and 200c of FIGS. 3, 5, 7A, and 7C may be applied to the optical tracking device 1000 of the present embodiment. Furthermore, the structures of all the curved pattern markers, which have at least two lens units and are capable of focusing the incident light onto the curved patterns of the pattern unit, may be applied to the optical tracking device 1000 of the present embodiment.

An image-forming unit 500 may receive parallel light for the curved patterns emitted from the curved pattern marker 100 so as to form images of the curved patterns as enlarged pattern images. The image-forming unit 500 may include a lens unit 510 and a sensor unit 520. The lens unit 510 may receive and enlarge parallel light of curved patterns. The sensor unit 520 is capable of forming curved patterns enlarged through the lens unit 510 as pattern images. For example, the image-forming unit 500 may be a camera.

The processor 600 may calculate the spatial position and orientation of the curved pattern marker 100 using the pattern images of the curved patterns formed on the image-forming unit 500. The details thereof are described as an example in non-published Korean Patent Application No. 10-2016-0101377 incorporated herein.

The optical tracking device 1000 of the present embodiment is provided with one curved pattern marker 100 and one image-forming unit 500, but the number of curved pattern markers 100 and image-forming units 500 is not limited to one. For example, a plurality of curved pattern markers 100 and a plurality of image-forming units 500 may be provided. Accordingly, the spatial position and orientation of an object may be calculated more precisely. For example, when the number of curved pattern markers 100 and the number of image-forming units 500 are increased, the spatial position and orientation of an object may be calculated more precisely through complex calculations.

While the present disclosure has been described with reference to the embodiments illustrated in the drawings, it will be understood by those skilled in the art that various modifications and other equivalent embodiments can be made without departing from the spirit and scope of the present disclosure. Accordingly, the true technical scope of the present disclosure should be determined by the technical idea of the appended claims.

What is claimed is:

1. A curved pattern marker comprising:
    a first lens unit including at least one lens having an incident surface and configured to emit incident light within a target range, the first lens unit being formed such that a light parallel to an optical axis among the incident light is perpendicularly incident on the incident surface;
    a pattern unit having a curved pattern formed therein; and
    a second lens unit disposed between the first lens unit and the pattern unit, and configured to adjust the light emitted from the first lens unit such that the light emitted from the first lens unit is focused on the curved pattern,
    wherein the first lens unit includes a first lens, a second lens, and a third lens sequentially coupled to each other in a direction toward the second lens unit, and
    the second lens unit further includes a fourth lens coupled to a curved lens in a direction toward the first lens unit.

2. The curved pattern marker of claim 1, wherein the curved pattern marker emits a light reflected from the pattern unit to be parallel to the incident light using the first lens unit and the second lens unit.

3. The curved pattern marker of claim 1, further comprising:
    an aperture disposed in front of the incident surface of the first lens unit and configured to limit a cross-sectional area through which the light is incident on the incident surface of the first lens unit.

4. The curved pattern marker of claim 3, wherein the incident surface of the first lens unit is a plane parallel to an opening face of the aperture.

5. The curved pattern marker of claim 3, further comprising:

a third lens unit disposed in front of the aperture and configured to condense the incident light to the aperture.

6. The curved pattern marker of claim 1, wherein the target range has an area larger than an area of an emitting surface of the first lens unit.

7. The curved pattern marker of claim 1, wherein the target range has an area larger than an area of an emitting surface of the first lens unit and smaller than or equal to an incident surface of the second lens unit.

8. The curved pattern marker of claim 1, wherein the first lens unit has a structure in which an incident surface of the second lens is coupled to an emitting surface of the first lens and an incident surface of the third lens is coupled to an emitting surface of the second lens, and the second lens unit has a structure in which an incident surface of the curved lens is coupled to an emitting surface of the fourth lens, and the fourth lens is disposed apart from the third lens.

9. The curved pattern marker of claim 8, wherein an incident surface of the fourth lens has a curvature smaller than a curvature of the emitting surface of the fourth lens, and the light emitted from the first lens unit is focused on the curved pattern through the fourth lens and the curved lens.

10. The curved pattern marker of claim 9, wherein an emitting surface of the curved lens has a curvature which is substantially equal to a curvature of the pattern unit, and the pattern unit is bonded to the emitting surface of the curved lens.

11. The curved pattern marker of claim 1, wherein a refractive index and a shape of incident surface and emitting surface of each of the first to fourth lenses and the curved lens are different from each other according to a curvature and a size of the curved pattern.

12. The curved pattern marker of claim 1, wherein
the curved lens is disposed apart from the third lens, and
a light emitted from the third lens is focused on the curved pattern through the curved lens.

13. The curved pattern marker of claim 1, further comprising:

a third lens unit disposed in a first direction opposite to a direction in which the second lens unit is disposed with respect to the first lens unit and including at least one lens; and a fourth lens unit disposed in the first direction from the third lens unit.

14. The curved pattern marker of claim 13, wherein the third lens unit includes a fifth lens and a sixth lens sequentially coupled in the first direction, and the fourth lens unit includes a seventh lens disposed apart from the fifth lens in the first direction.

15. The curved pattern marker of claim 1, further comprising:

a holder configured to accommodate the first lens unit and the second lens unit, wherein the pattern unit is bonded to an emitting surface of a curved lens or is bonded to an inner surface of the holder that faces the emitting surface of the curved lens.

16. The curved pattern marker of claim 1, wherein the pattern unit includes an adhesive layer, a pattern layer on which the curved pattern is formed, and a reflective layer.

* * * * *